United States Patent
Becker et al.

(10) Patent No.: US 12,059,211 B2
(45) Date of Patent: Aug. 13, 2024

(54) TECHNIQUES FOR PATIENT-SPECIFIC MORPHING OF VIRTUAL BOUNDARIES

(71) Applicant: MAKO Surgical Corp., Weston, FL (US)

(72) Inventors: Hans-Ulrich Becker, Muellheim (DE); Patrick Roessler, Merzhausen (DE); José Luis Moctezuma de la Barrera, Freiburg (DE)

(73) Assignee: MAKO Surgical Corp., Weston, FL (US)

( * ) Notice: Subject to any disclaimer, the term of this patent is extended or adjusted under 35 U.S.C. 154(b) by 66 days.

(21) Appl. No.: 18/073,715

(22) Filed: Dec. 2, 2022

(65) Prior Publication Data
US 2023/0105049 A1   Apr. 6, 2023

Related U.S. Application Data

(63) Continuation of application No. 16/710,707, filed on Dec. 11, 2019, now Pat. No. 11,547,482.
(Continued)

(51) Int. Cl.
*G06T 7/73* (2017.01)
*A61B 34/10* (2016.01)
*G06T 7/00* (2017.01)

(52) U.S. Cl.
CPC ............ *A61B 34/10* (2016.02); *G06T 7/0012* (2013.01); *G06T 7/73* (2017.01); *A61B 2034/102* (2016.02);
(Continued)

(58) Field of Classification Search
CPC ..................................................... A61B 34/19
See application file for complete search history.

(56) References Cited

U.S. PATENT DOCUMENTS

| 8,126,234 B1 | 2/2012 | Edwards et al. |
| 8,234,097 B2 | 7/2012 | Steines et al. |

(Continued)

FOREIGN PATENT DOCUMENTS

| WO | 2010019463 A1 | 2/2010 |
| WO | 2011041428 A2 | 4/2011 |

(Continued)

OTHER PUBLICATIONS

International Search Report for Application No. PCT/US2019/065985 dated Mar. 17, 2020, 5 pages.
(Continued)

*Primary Examiner* — Oneal R Mistry
(74) *Attorney, Agent, or Firm* — Howard & Howard Attorneys PLLC

(57) ABSTRACT

Surgical systems, computer-implemented methods, and software programs for producing a patient-specific virtual boundary configured to constrain movement and/or operation of a surgical tool in response to the surgical tool interacting with the patient-specific virtual boundary. The implementations include obtaining a generic virtual boundary including a generic surface with a generic edge, and positioning the generic virtual boundary relative to a virtual anatomical model such that the generic surface intersects the virtual anatomical model. The implementations include computing an intersection of the generic surface and the virtual anatomical model to define a cross-sectional contour of the virtual anatomical model, and morphing the generic edge to the cross-sectional contour to produce a customized surface with a patient-specific edge. The implementations include generating a customized face extending from, and along, the patient-specific edge, and producing the patient-specific virtual boundary by merging the customized surface and the customized face.

20 Claims, 13 Drawing Sheets

Related U.S. Application Data

(60) Provisional application No. 62/779,191, filed on Dec. 13, 2018.

(52) U.S. Cl.
CPC .............. *G06T 2207/20036* (2013.01); *G06T 2207/20116* (2013.01); *G06T 2207/30052* (2013.01); *G06T 2210/21* (2013.01); *G06T 2210/44* (2013.01)

(56) References Cited

U.S. PATENT DOCUMENTS

| | | | |
|---|---|---|---|
| 8,382,765 | B2 | 2/2013 | Axelson et al. |
| 8,532,806 | B1 | 9/2013 | Masson |
| 8,617,171 | B2 | 12/2013 | Park et al. |
| 8,731,885 | B2 | 5/2014 | Iannotti et al. |
| 8,884,618 | B2 | 11/2014 | Mahfouz |
| 8,939,982 | B2 | 1/2015 | Chellaoui |
| 9,008,757 | B2 | 4/2015 | Wu |
| 9,060,788 | B2 | 6/2015 | Bollinger |
| 9,089,380 | B2 | 7/2015 | Suttin et al. |
| 9,119,655 | B2 | 9/2015 | Bowling et al. |
| 9,275,192 | B2 | 3/2016 | Kang et al. |
| 9,326,780 | B2 | 5/2016 | Wong et al. |
| 9,345,548 | B2 | 5/2016 | Schoenefeld et al. |
| 9,427,320 | B2 | 8/2016 | Meridew |
| 9,597,201 | B2 | 3/2017 | Bollinger |
| 9,681,956 | B2 | 6/2017 | Al Hares et al. |
| 9,937,011 | B2 | 4/2018 | Yosibash et al. |
| 9,987,092 | B2 | 6/2018 | Hladio et al. |
| 10,004,565 | B2 | 6/2018 | Kang et al. |
| 10,085,839 | B2 | 10/2018 | Wong et al. |
| 10,102,309 | B2 | 10/2018 | McKinnon et al. |
| 10,130,378 | B2 | 11/2018 | Bryan |
| 10,166,109 | B2 | 1/2019 | Ferko |
| 10,258,352 | B2 | 4/2019 | Iannotti et al. |
| 10,265,127 | B2 | 4/2019 | Jaramaz et al. |
| 10,321,961 | B2 | 6/2019 | McCarthy et al. |
| 10,376,270 | B2 | 8/2019 | Eash |
| 10,383,765 | B2 * | 8/2019 | Alvarez ................. A61B 34/30 |
| 10,456,262 | B2 | 10/2019 | Mistry |
| 10,512,496 | B2 | 12/2019 | Iannotti et al. |
| 10,537,343 | B2 | 1/2020 | Fritzinger |
| 10,603,056 | B2 | 3/2020 | Wiebe, III et al. |
| 10,631,932 | B2 | 4/2020 | Mckinnon et al. |
| 2007/0276501 | A1 | 11/2007 | Betz et al. |
| 2008/0273777 | A1 * | 11/2008 | Luboz ....................... G06T 7/64 382/130 |
| 2009/0149977 | A1 | 6/2009 | Schendel |
| 2010/0153081 | A1 | 6/2010 | Bellettre et al. |
| 2010/0274534 | A1 | 10/2010 | Steines et al. |
| 2011/0190899 | A1 | 8/2011 | Pierce et al. |
| 2011/0214279 | A1 | 9/2011 | Park et al. |
| 2011/0295565 | A1 | 12/2011 | Ozen |
| 2012/0010711 | A1 | 1/2012 | Antonyshyn et al. |
| 2012/0030429 | A1 | 2/2012 | Synge |
| 2012/0078259 | A1 | 3/2012 | Meridew |
| 2012/0123423 | A1 | 5/2012 | Fryman |
| 2012/0271366 | A1 | 10/2012 | Katrana et al. |
| 2012/0310364 | A1 | 12/2012 | Li et al. |
| 2013/0006250 | A1 | 1/2013 | Metzger et al. |
| 2013/0035690 | A1 | 2/2013 | Mittelstadt et al. |
| 2013/0211792 | A1 | 8/2013 | Kang et al. |
| 2013/0236874 | A1 | 9/2013 | Iannotti et al. |
| 2014/0180290 | A1 | 6/2014 | Otto et al. |
| 2014/0221825 | A1 | 8/2014 | Mahfouz et al. |
| 2014/0244220 | A1 | 8/2014 | McKinnon et al. |
| 2014/0276949 | A1 | 9/2014 | Staunton et al. |
| 2015/0080717 | A1 | 3/2015 | Ferko |
| 2015/0088142 | A1 | 3/2015 | Gibson |
| 2015/0119987 | A1 | 4/2015 | Davignon et al. |
| 2015/0185846 | A1 | 7/2015 | Otto et al. |
| 2015/0335438 | A1 | 11/2015 | Pierce et al. |
| 2016/0015465 | A1 | 1/2016 | Steines et al. |
| 2016/0038243 | A1 | 2/2016 | Miller et al. |
| 2016/0074124 | A1 | 3/2016 | Fitz et al. |
| 2016/0089057 | A1 * | 3/2016 | Jia ....................... A61B 5/053 600/424 |
| 2016/0100773 | A1 | 4/2016 | Ching et al. |
| 2016/0155236 | A1 | 6/2016 | Davey |
| 2016/0274571 | A1 | 9/2016 | Lavallee et al. |
| 2017/0007331 | A1 | 1/2017 | Couture et al. |
| 2017/0056022 | A1 | 3/2017 | Cheal et al. |
| 2017/0086859 | A1 | 3/2017 | Couture |
| 2017/0231709 | A1 | 8/2017 | Gupta et al. |
| 2017/0252169 | A1 | 9/2017 | Alambeigi et al. |
| 2017/0273797 | A1 | 9/2017 | Gordon et al. |
| 2017/0296205 | A1 | 10/2017 | Iannotti et al. |
| 2017/0312032 | A1 * | 11/2017 | Amanatullah ......... G09B 23/30 |
| 2018/0153624 | A1 | 6/2018 | Hughes et al. |
| 2018/0228614 | A1 | 8/2018 | Lang et al. |
| 2018/0263782 | A1 | 9/2018 | Lang et al. |
| 2018/0303552 | A1 | 10/2018 | Ryan et al. |
| 2018/0325683 | A1 | 11/2018 | Logan et al. |
| 2018/0333207 | A1 | 11/2018 | Moctezuma De la Barrera |
| 2018/0349519 | A1 | 12/2018 | Schroeder |
| 2018/0353253 | A1 | 12/2018 | Bowling |
| 2018/0358120 | A1 | 12/2018 | Schoenefeld et al. |
| 2018/0360609 | A1 | 12/2018 | Steines et al. |
| 2019/0015119 | A1 | 1/2019 | Athwal et al. |
| 2019/0029757 | A1 | 1/2019 | Roh et al. |
| 2019/0133791 | A1 | 5/2019 | Yadav et al. |
| 2019/0142520 | A1 | 5/2019 | VanDyken |
| 2019/0146458 | A1 | 5/2019 | Roh et al. |
| 2019/0201005 | A1 | 7/2019 | Schoenefeld et al. |
| 2019/0223886 | A1 | 7/2019 | Fritzinger |
| 2019/0223887 | A1 | 7/2019 | Fritzinger et al. |
| 2019/0231431 | A1 | 8/2019 | Paszicsnyek |
| 2019/0290361 | A1 | 9/2019 | Shalayev et al. |
| 2019/0328534 | A1 | 10/2019 | Otto et al. |
| 2019/0380788 | A1 | 12/2019 | Becker et al. |
| 2020/0046518 | A1 | 2/2020 | Schoenefeld et al. |
| 2020/0188025 | A1 | 6/2020 | Becker et al. |

FOREIGN PATENT DOCUMENTS

| | | |
|---|---|---|
| WO | 2013101753 A1 | 7/2013 |
| WO | 2013170872 A1 | 11/2013 |
| WO | 2017200785 A1 | 11/2017 |

OTHER PUBLICATIONS

Stroud, Ian, "Abstract, Preface and Table of Contents of Boundary Representation Modeling Techniques", ISBN 1-84628-312-4, Springer, 2006, 18 pages.

* cited by examiner

TECHNIQUES FOR PATIENT-SPECIFIC MORPHING OF VIRTUAL BOUNDARIES

CROSS-REFERENCE TO RELATED APPLICATIONS

The subject application is a continuation of U.S. patent application Ser. No. 16/710,707, filed Dec. 11, 2019, which claims priority to and all the benefits of U.S. Provisional Patent Application No. 62/779,191, filed Dec. 13, 2018, the entire contents of each of the aforementioned applications being hereby incorporated by reference.

TECHNICAL FIELD

The present disclosure relates to techniques for generating a patient-specific virtual boundary for a surgical system.

BACKGROUND

Robotic systems are commonly used to perform surgical procedures and typically include a robot comprising a robotic arm and an end effector coupled to the robotic arm. Often, the end effector comprises a shaft with a milling burr coupled to the distal end of the shaft.

In a manual mode of operation, the robotic system senses forces/torques manually applied to the end effector by the user. The robotic system commands positioning of end effector to emulate motion expected from application of the sensed forces/torques. In autonomous modes, the robotic system commands the robot arm to move the end effector along a computer-defined milling path at least partially unassisted by the user. In either mode, a supplemental tracking system, such as optical localization, may be utilized to track positioning of the robot and the surgical site.

Total or partial knee arthroplasty involves milling or cutting diseased bone tissue and replacing the diseased bone with a physical implant. With prior techniques, a virtual implant model (corresponding to a physical implant) is selected preoperatively for planning the procedure. The virtual implant model defines an implant specific (not patient specific) shape. In other words, the virtual implant model is generic.

The virtual implant model is utilized to define a generic virtual boundary or constraint. For each implant model, a one-size fits all "implant specific" generic boundary exists, regardless for which patient the implant is planned. For this reason, implant specific virtual boundaries need to be designed for the allowable worst-case placement (i.e., that of greatest potential bone removal). Accordingly, prior virtual boundaries are not patient-specific.

Such issues are particularly evident in situations where the implant is an onlay/overhang type whereby the implant is located on top of the bone (not placed into depressions of the bone) and partially hangs over the edge of the bone. In such situations, adjacent soft tissue surrounds the overhang region making milling particularly challenging. Because the generic virtual boundary is designed "worst-case" and not truly patient-specific, the burr may incidentally enter soft tissue regions without leaving the generic virtual boundary. To mitigate this problem, surgeons conventionally rely solely on visual inspection to avoid cutting soft tissue thereby introducing the possibility of manual error.

When intending to machine in a region of restricted access, such as machining posterior femur knee anatomy with the tibia bone nearby, worst-case planning may potentially result in removal of more of the femur bone than necessary. Furthermore, air-cutting can increase the possibility of the end effector shaft colliding with the nearby tibia bone.

Conventional techniques are also limited to pre-operative implant planning and pre-operative generation of the virtual boundary, thereby providing little flexibility to make intra-operative modifications to the same. Conventional techniques also require a significant amount of computational time to generate the bone model and compute the virtual boundary. During the surgical procedure, time is of the essence and the workflow cannot be prolonged to await computation of an updated surgical plan. For this reason, conventional techniques are also not suitably adaptable to the intraoperative workflow because they have not provided a solution to enable rapid updating of the plan without significant delays required for computation.

As such, there is a need in the art for systems and methods for addressing at least the aforementioned problems.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a computer-implemented surgical planning method is provided, comprising: obtaining a generic virtual boundary comprising a generic surface with a generic edge; positioning the generic virtual boundary relative to a virtual anatomical model such that the generic surface intersects the virtual anatomical model; computing an intersection of the generic surface and the virtual anatomical model to define a cross-sectional contour of the virtual anatomical model; morphing the generic edge to the cross-sectional contour to produce a customized surface with a patient-specific edge; generating a customized face extending from, and along, the patient-specific edge; producing a patient-specific virtual boundary by merging the customized surface and the customized face; and configuring the patient-specific virtual boundary for providing a constraint on movement and/or operation of a surgical tool in response to the surgical tool interacting with the patient-specific virtual boundary.

According to a second aspect, a non-transitory computer readable medium is provided comprising instructions, which when executed by one or more processors, are configured to: obtain a generic virtual boundary comprising a generic surface with a generic edge; position the generic virtual boundary relative to a virtual anatomical model such that the generic surface intersects the virtual anatomical model; compute an intersection of the generic surface and the virtual anatomical model to define a cross-sectional contour of the virtual anatomical model; morph the generic edge to the cross-sectional contour to produce a customized surface with a patient-specific edge; generate a customized face that extends from, and along, the patient-specific edge; produce a patient-specific virtual boundary by merger of the customized surface and the customized face; and configure the patient-specific virtual boundary to provide a constraint on movement and/or operation of a surgical tool responsive to interaction between the surgical tool and the patient-specific virtual boundary.

According to a third aspect, a surgical system is provided, comprising: a surgical tool; and one or more controllers coupled to the surgical tool and being configured to: obtain a generic virtual boundary comprising a generic surface with a generic edge; position the generic virtual boundary relative to a virtual anatomical model such that the generic surface intersects the virtual anatomical model; compute an intersection of the generic surface and the virtual anatomical model to define a cross-sectional contour of the virtual anatomical model; morph the generic edge to the cross-sectional contour to produce a customized surface with a patient-specific edge; generate a customized face that extends from, and along, the patient-specific edge; produce a patient-specific virtual boundary by merger of the customized surface and the customized face; and configure the patient-specific virtual boundary to provide a constraint on movement and/or operation of a surgical tool responsive to interaction between the surgical tool and the patient-specific virtual boundary.

Further provided is a method for operating the tool of the surgical system relative to the patient-specific virtual boundary of any of the examples described herein.

The system, method and software program provide technical solutions to several technical problems associated with conventional milling planning and execution.

The techniques described herein enable morphing the generic virtual boundary to conform to the feature of the anatomical model. Hence, the generic constraint is made into a patient-specific constraint.

Moreover, the techniques described herein enable intraoperative or on-the-fly planning and generation of the patient-specific virtual boundary. Thus, for example, if the surgeon is not satisfied with the pre-operative implant plan, or if unforeseen circumstances arise, the surgeon can freely update the implant position intraoperatively. By use of the software, the system can perform the aforementioned morphing on-the fly. The constraint morphing techniques are suitably adapted to be used in the operating room, by providing a solution to enable rapid updating of the plan without significant delays required for computation. An updated patient-specific plan, including an updated virtual boundary, can quickly be generated intraoperatively. The techniques described herein can also provide such advantages preoperatively.

With the techniques described herein, milling relative to the patient-specific defined virtual boundary will be constrained to the hard tissue (e.g., bone) without affecting surrounding tissue. For these reasons, the system, method and software program provide a truly "patient specific" solution.

With this improved approach, a wide array of milling procedures based on the patient-specific virtual boundary can be executed with a high degree of accuracy. For instance, milling is possible for insertion of the onlay/overhang type implant as well as an inlay type implant (i.e., an implant that is inserted into a resected pocket of the bone and the implant is surrounded by a rim of bone). The virtual boundary is customized to account for the overhang region such that surrounding soft tissue can be preserved. The patient-specific virtual boundary can provide these advantages in both manual and autonomous modes of tool operation.

Moreover, the techniques described herein reduce the likelihood of collision between the end effector shaft and the bone. For example, if milling is performed on the femur bone, collisions of the shaft with the tibia bone is avoided because only the minimal required amount of the femur bone is removed, thus avoiding the interaction with the nearby tibia bone possible with generic virtual boundaries.

The system, method, and software program may exhibit advantages and provide technical solutions other than those described herein.

DESCRIPTION OF THE DRAWINGS

Other aspects, features, and advantages of the present invention will become more fully apparent from the detailed description, the appended claims, and the accompanying drawings wherein like reference numerals identify similar or identical elements.

DETAILED DESCRIPTION

I. Overview of the Robotic Surgical System

Referring to the FIGS. 1 and 2, wherein like numerals indicate like or corresponding parts throughout the several views, a robotic surgical system 10 (hereinafter "system") and components thereof are illustrated. Further provided is a non-transitory computer readable medium comprising instructions, which when executed by one or more processors implement a software program for the robotic surgical system 10 as well as methods for using the software program. Aspects of the software program and method are addressed in the subsequent section below.

Figure 1:
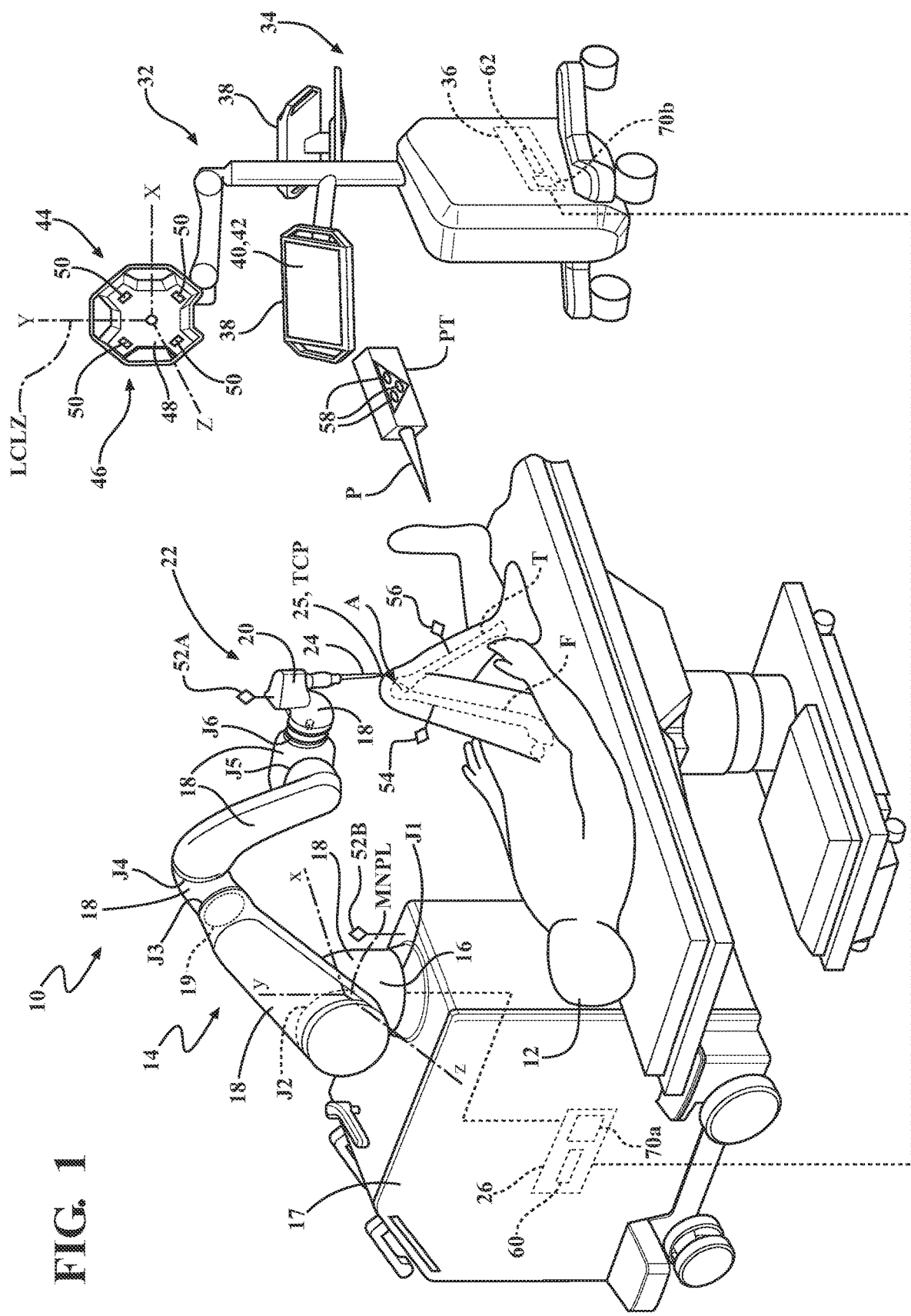
FIG. 1 is one example of a robotic surgical system employing the patient-specific constraint morphing techniques described herein.

As shown in FIG. 1, the system 10 is a robotic surgical system for treating surgical site or anatomical volume (A) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves partial or total knee or hip replacement surgery. In one example, the system 10 is designed to cut away material to be replaced by surgical implants, such as hip and knee implants, including unicompartmental, bicompartmental, multicompartmental, or total knee implants. Some of these types of implants are shown in U.S. Patent Application Publication No. 2012/0030429, entitled, "Prosthetic Implant and Method of Implantation," the disclosure of which is hereby incorporated by reference. The system 10 and techniques disclosed herein may be used to perform other procedures, surgical or non-surgical, or may be used in industrial applications or other applications where robotic systems are utilized.

The system 10 includes a manipulator 14. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints (J) and a plurality of joint encoders 19 located at the joints (J) for determining position data of the joints (J). For simplicity, only one joint encoder 19 is illustrated in FIG. 1, although other joint encoders 19 may be similarly illustrated. The manipulator 14 according to one example has six joints (J1-J6) implementing at least six-degrees of freedom (DOF) for the manipulator 14. However, the manipulator 14 may have any number of degrees of freedom and may have any suitable number of joints (J) and redundant joints (J).

The manipulator 14 need not require 'joint' encoders 19 but may alternatively or additionally utilize motor encoders. Also, the manipulator 14 need not require rotary joints, but may alternatively or additionally utilize one or more prismatic joints.

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or cart 17. The manipulator 14 and/or manipulator cart 17 house a manipulator computer 26, or other type of control unit. In other examples, the manipulator 14 can be a hand-held where the base 16 is a portion of the tool 20 is held stable while the tool tip follows the path.

A surgical tool 20 (hereinafter "tool") couples to the manipulator 14 and is movable relative to the base 16 to interact with the anatomy (A). The tool 20 is or forms part of an end effector 22 in certain embodiments. The tool 20 may be grasped by the operator. One exemplary arrangement of the manipulator 14 and the tool 20 is described in U.S. Pat. No. 9,119,655, entitled, "Surgical Manipulator Capable of Controlling a Surgical Tool in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference. Other examples of tools 20 comprise drills, saws, planar cut guides, drill guides, or the like.

The tool 20 includes an energy applicator 24 designed to contact and remove the tissue of the patient 12 at the surgical site. In one example, the energy applicator 24 is a burr 25. The burr 25 may be substantially spherical and comprise a spherical center, radius (r) and diameter. Alternatively, the energy applicator 24 may be a drill bit, a saw blade, an ultrasonic vibrating tip, or the like. The tool 20 and/or energy applicator 24 may comprise any geometric feature, e.g., perimeter, circumference, radius, diameter, width, length, volume, area, surface/plane, range of motion envelope (along any one or more axes), etc. As will be described below, the geometric feature may be considered in certain features relating to offsets for virtual constraints, and the like.

The tool 20 may comprise a tool center point (TCP), which in one example, is a predetermined reference point defined at the energy applicator 24. The TCP has a known, or able to be calculated (i.e., not necessarily static), pose relative to other coordinate systems of the manipulator 14. The geometry of the energy applicator 24 is known in or defined relative to the TCP coordinate system. The TCP may be located at the spherical center of the burr 25 of the tool 20 such that only one point is tracked. The TCP may be defined according to various manners depending on the configuration of the energy applicator 24. The manipulator 14 could have motor encoders, or any other non-encoder position sensing method, to enable pose of the TCP can be determined. The manipulator 14 may use joint measurements to determine TCP pose and/or could employ techniques to measure TCP pose directly. The control of the tool 20 is not limited to a center point. For example, any suitable primitives, meshes, etc., can be used to represent the tool 20.

Figure 2:
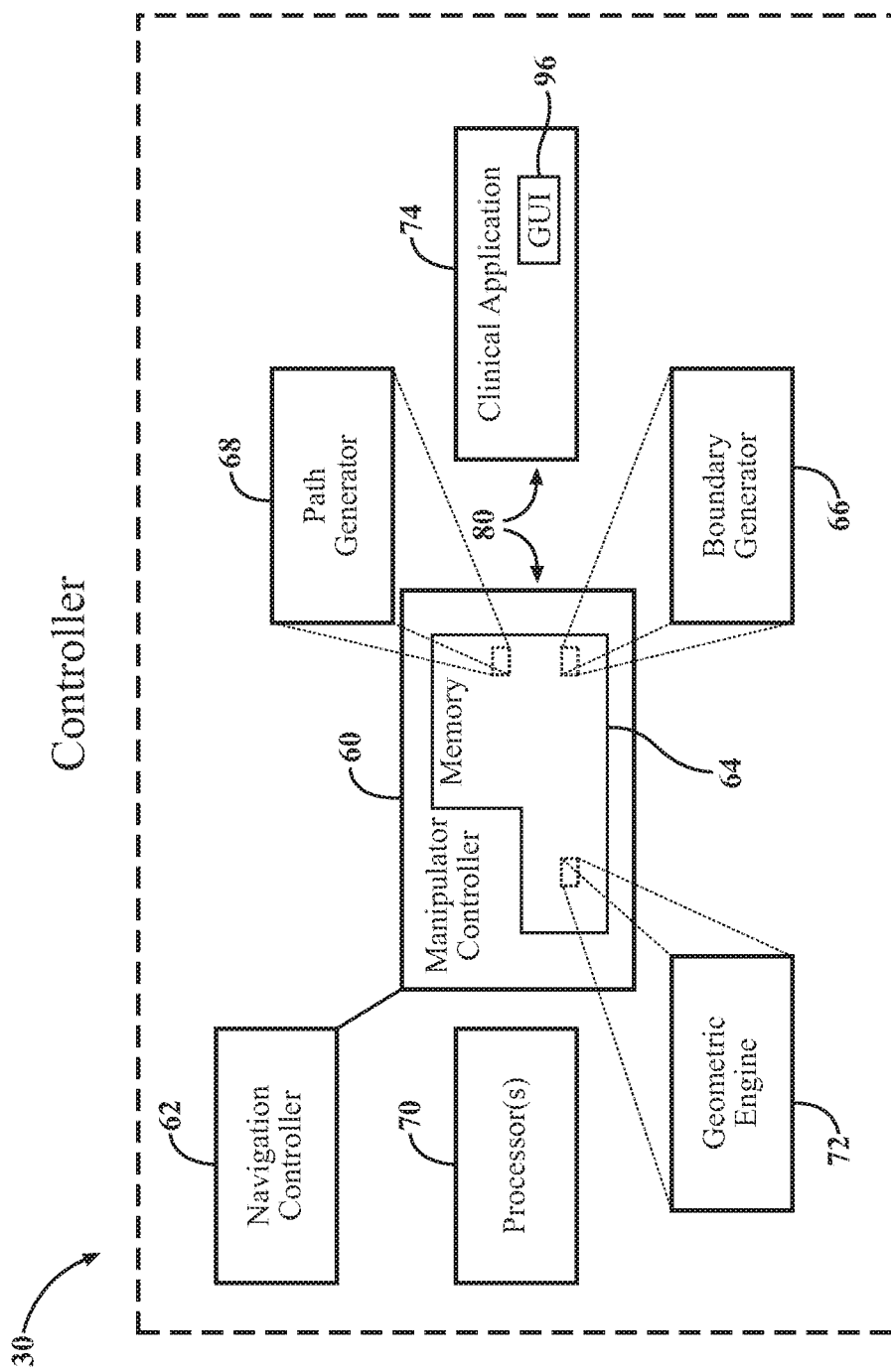
FIG. 2 is an example configuration of one or more controllers of the robotic surgical system, including a software program configured to implement the patient-specific constraint morphing techniques described herein.

Referring to FIG. 2, the system 10 includes a controller 30. The controller 30 includes software and/or hardware for controlling the manipulator 14. The controller 30 directs the motion of the manipulator 14 and controls a state (position and/or orientation) of the tool 20 with respect to a coordinate system. The controller 30 can control (linear or angular) velocity, acceleration, or other derivatives of motion of the tool 20. In one example, the coordinate system is the manipulator coordinate system MNPL, as shown in FIG. 1. One example of the manipulator coordinate system MNPL is described in U.S. Pat. No. 9,119,655, entitled, "Surgical Manipulator Capable of Controlling a Surgical Tool in Multiple Modes," the disclosure of which is hereby incorporated by reference. Further aspects and capabilities of the controller 30 are described below.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformations.

The navigation system 32 includes a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. One or more input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50.

The navigation system 32 includes one or more trackers. In one example, the trackers include a pointer tracker PT, one or more manipulator trackers 52, a first patient tracker 54, and a second patient tracker 56. In the illustrated example of FIG. 1, the manipulator tracker 52 is firmly attached to the tool 20 (i.e., tracker 52A), the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer P used for registering the anatomy to the localizer coordinate system LCLZ. The manipulator tracker 52 may be affixed to any suitable component of the manipulator 14, in addition to, or other than the tool 20, such as the base 16 (i.e., tracker 52B), or any one or more links 18 of the manipulator 14. The trackers 52, 54, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the item associated therewith.

Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of each of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

Although one example of the navigation system 32 is shown in the Figures, the navigation system 32 may have any other suitable configuration for tracking the manipulator 14 and the patient 12. In another example, the navigation system 32 and/or localizer 44 are ultrasound-based. For example, the navigation system 32 may comprise an ultrasound imaging device coupled to the navigation computer 36. The ultrasound imaging device images any of the aforementioned objects, e.g., the manipulator 14 and the patient 12, and generates state signals to the controller 30 based on the ultrasound images. The ultrasound images may be 2-D, 3-D, or a combination of both. The navigation computer 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation computer 36. The manipulator 14 and the patient 12 may comprise RF emitters or transponders attached thereto. The RF emitters or transponders may be passive or actively energized. The RF transceiver transmits an RF tracking signal and generates state signals to the controller 30 based on RF signals received from the RF emitters. The navigation computer 36 and/or the controller 30 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56 as shown in FIG. 1.

In yet another example, the navigation system 32 and/or localizer 44 are electromagnetically based. For example, the navigation system 32 may comprise an EM transceiver coupled to the navigation computer 36. The manipulator 14 and the patient 12 may comprise EM components attached thereto, such as any suitable magnetic tracker, electromagnetic tracker, inductive tracker, or the like. The trackers may be passive or actively energized. The EM transceiver generates an EM field and generates state signals to the controller 30 based upon EM signals received from the trackers. The navigation computer 36 and/or the controller 30 may analyze the received EM signals to associate relative states thereto. Again, such navigation system 32 examples may have structural configurations that are different than the navigation system 32 configuration as shown throughout the Figures.

The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

As shown in FIG. 2, the controller 30 further includes one or more software programs and/or software modules. The software modules may be part of the program or programs that operate on the manipulator computer 26, navigation computer 36, or a combination thereof, to process data to assist with control of the system 10. The software programs and/or modules includes computer readable instructions stored in non-transitory memory 64 on the manipulator computer 26, navigation computer 36, or a combination thereof, to be executed by one or more processors 70a, 70b of the computers 26, 36. The memory 64 may be any suitable configuration of memory, such as RAM, non-volatile memory, etc., and may be implemented locally or from a remote database. Additionally, software modules for prompting and/or communicating with the operator may form part of the program or programs and may include instructions stored in memory 64 on the manipulator computer 26, navigation computer 36, or a combination thereof. The operator may interact with any of the input devices 40, 42 and the displays 38 to communicate with the software modules. The user interface software may run on a separate device from the manipulator computer 26 and navigation computer 36.

The controller 30 includes a manipulator controller 60 for processing data to direct motion of the manipulator 14. In one example, as shown in FIG. 1, the manipulator controller is implemented on the manipulator computer 26. The controller 30 further includes a navigation (or localization) controller 62 for communicating the state data relating to the femur F, tibia T, and manipulator 14 to the manipulator controller 60. The navigation controller 62 is also configured to process/analyze the measurements from the camera and trackers to compute the state data. This processing could be done elsewhere on the system, including inside the camera itself. The manipulator controller 60 receives and processes the state data provided by the navigation controller 62 to direct movement of the manipulator 14. As shown in FIG. 1, the navigation controller 62 is implemented on the navigation computer 36. The controllers 60 and 62 handle the real-time control and algorithms.

As shown in FIG. 2, the controller 30 includes a boundary generator 66. The boundary generator 66 is a software program or module that generates a planar or non-planar virtual boundary for constraining movement and/or operation of the tool 20. Such virtual boundaries may also be referred to as virtual meshes, virtual constraints, or the like. The virtual boundaries may be defined with respect to an anatomical model, such as a 3-D bone model. The anatomical model (AM) is registered to the one or more patient trackers 54, 56 such that the virtual boundaries become associated with to the anatomical model (AM). The manipulator controller 60 executes the virtual boundaries 70 by tracking the state of the tool 20 relative to the virtual boundaries. In one example, the state of the TCP is measured relative to the virtual boundaries for purposes of determining haptic forces that are applied to a virtual model via a physics simulation. The results of the simulation are commanded to the manipulator 14. The controller 30 controls/positions the manipulator 14 in a manner that emulates the way a physical handpiece would respond to the user and virtual haptic forces. The boundary generator 66 may be implemented on the manipulator controller 60. Alternatively, the boundary generator 66 may be implemented on other components, such as the navigation controller 62.

As will be described in the subsequent section, the virtual boundaries are generated using a patient-specific morphing technique. However, not all virtual boundaries utilized by the system must be patient-specific. Some boundaries may be implant-specific or generic. It is also not necessary to have patient-specific virtual boundaries even for the case of patient-specific tool paths. Example techniques for generating a patient-specific tool path, which can be utilized with the techniques described herein, is described in U.S. Provisional Patent Application No. 62/685,476, filed on Jun. 15, 2018, the contents of which is incorporated by reference herein in its entirety.

For implant-specific scenarios, the boundary generator 66 does not need to be part of the system 10 or controller 30, but rather the boundaries can be manually generated offline for each possible implant size, and the resulting boundaries stored with the software. For patient-specific scenarios, the boundary generator 66 may be part of a clinical application 74 (described below) that handles user interaction, rather than part of the controller 30 or manipulator controller 60.

Optionally, a milling path generator 68 is another software program or module run by the controller 30. In one example, the milling path generator 68 is run by the manipulator controller 60. The milling path generator 68 generates a milling path for the tool 20 to traverse, such as for removing sections of the anatomy to receive an implant. It should be understood that the term "milling path" generally refers to the path of the tool 20 in the vicinity of the target site for milling the anatomy and is not intended to require that the tool 20 be operably milling the anatomy throughout the entire duration of the path. For instance, the milling path may comprise sections or segments where the tool 20 transitions from one location to another without executing milling.

A geometric engine 72 is another software program or module run by the controller 30. The geometric engine 72 may be a sub-set of the milling path generator 68 or boundary generator 66 or may be a program or module separate from or encompassing the same. The geometric engine 72 will be described in detail below.

The boundary generator 66, milling path generator 68, and geometric engine 72 may be sub-sets of a software program 80. Alternatively, each may be software programs that operate separately and/or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 66, milling path generator 68, and/or geometric engine 72. The software program 80 can be implemented on the manipulator controller 60, navigation controller 62, or combination thereof.

In some examples, the virtual boundaries and/or milling paths may be generated offline rather than on the manipulator computer 26 or navigation computer 36. Thereafter, the virtual boundaries and/or milling paths may be utilized at runtime by the manipulator controller 60.

Examples for generating the milling path are explained in U.S. Pat. No. 9,119,655, entitled, "Surgical Manipulator Capable of Controlling a Surgical Tool in Multiple Modes," and U.S. Provisional Patent Application No. 62/685,476, filed Jun. 15, 2018, entitled "Techniques For Patient-Specific Milling Path Generation," the disclosures of which are hereby incorporated by reference in their entirety.

A clinical application 74 is provided to handle the user interaction. The clinical application 74 handles many aspects of user interaction and coordinates the surgical workflow, including intraoperative or pre-operative planning, implant placement, registration, bone preparation visualization, and post-operative evaluation of implant fit, etc. The clinical application 74 is configured to output to the displays 38. The clinical application 74 either may run on its own separate processor or may run alongside controller 62 on the navigation computer 36. In one example, the clinical application 74 interfaces with the boundary generator 66, the path generator 68 and/or geometric engine 72 after implant placement is set by the user (preoperatively or intraoperatively), and then sends the tool path returned by the path generator 68 to controller 60 for execution. The manipulator controller 60 executes a tool path. The clinical application 74, and more specifically a graphical user interface (GUI) 96 employed by the clinical application 74, are described in further detail below.

The system 10 may be operated in an autonomous mode. In the autonomous mode, the input for the primary movement of the TCP for bone resection is based off the milling path. In the autonomous mode, the manipulator 14 is capable of moving the tool 20 free of operator assistance along the milling path. Free of operator assistance may mean that an operator is not required to physically contact the tool 20 to apply force to move the tool 20. Instead, the operator may use some form of control to remotely manage starting and stopping of movement. For example, the operator may hold down a button of a remote control to start movement of the tool 20 and release the button to stop movement of the tool 20. Alternatively, the operator may press a button to start movement of the tool 20 and press a button to stop movement of the tool 20. In some modes of operation, the milling path automatically advances the TCP position, but the orientation of the tool 20 can be adjusted by the user by physically applying forces. During autonomous execution, boundary constraints may stay active as a risk mitigation against any issues/errors in the tool path.

The system 10 can also be operated in the manual mode. In the manual mode, the input for the primary movement of the TCP for bone resection is based off the user-applied forces/torques. Here, the operator manually directs, and the manipulator 14 controls, movement of the tool 20 and, in turn, the energy applicator 24 at the surgical site. The operator physically contacts the tool 20 to cause movement of the tool 20. The manipulator 14 monitors the forces and torques placed on the tool 20 by the operator in order to position the tool 20. A sensor that is part of the manipulator 14, such as a force-torque transducer, measures these forces and torques. In response to the applied forces and torques, the manipulator 14 mechanically moves the tool 20 in a manner that emulates the movement that would have occurred based on the forces and torques applied by the operator. Movement of the tool 20 in the manual mode is also constrained in relation to the virtual constraints generated by the boundary generator 66 and/or path generator 68.

II. Patient-Specific Constraint Morphing

Described herein are advanced techniques for generating a patient-specific virtual boundary (PS-VB) for an anatomical model (AM). This is accomplished by adjusting a generic virtual boundary (G-VB) to the patient's anatomy. More specifically, the techniques for generating the patient-specific virtual boundary (PS-VB) comprise positioning a generic virtual boundary (G-VB) proximate to a feature of the anatomical model (AM) and generating the patient-specific virtual boundary (PS-VB) by morphing the generic virtual boundary (G-VB) to conform to the feature of the anatomical model (AM). The feature of the anatomical model (AM) may comprise a cross-sectional contour of the anatomical model (AM) based on an intersection of the anatomical model (AM) with the generic virtual boundary (G-VB).

The techniques described herein provide technical solutions for enabling intraoperative updating of a surgical plan on-the-fly using an approach that is fast and accurately tailored to the anatomy of the specific patient, rather than designed based entirely on a generic geometry. While the techniques focus predominately on an intraoperative solution, the techniques may also be utilized for making an initial pre-operative plan or making pre-operative adjustments to an initial plan.

The advantages of the patient-specific virtual boundary (PS-VB) can be realized in autonomous and manual modes of tool operation. For instance, in the autonomous mode, the system 10 can constrain the tool 20 according to a patient-specific tool path generated to conform to the patient-specific virtual boundary (PS-VB), such as described in U.S. Provisional Patent Application No. 62/685,476, filed on Jun. 15, 2018, the contents of which are incorporated by reference herein in its entirety. In the manual mode, the robotic system commands positioning of tool 20 to emulate motion expected from application of the sensed forces/torques applied to the tool 20 by the user. The forces/torques are modeled with the patient-specific virtual boundary (PS-VB) taken into account. The commanded positioning of tool 20, and hence, the emulated motion is limited such that the patient-specific virtual boundary (PS-VB) is not breached by the tool 20.

Moreover, as used herein, the term "morph" and any variation thereof is not limited to changes from one geometric form to another by gradual computer-executed steps that are visible to the user. The patient-specific virtual boundary (PS-VB) can be generated without the user visualizing the steps needed to form the same. Moreover, the steps in forming patient-specific virtual boundary (PS-VB) do not need to occur directly based off the actual geometry of the generic virtual boundary (G-VB). Instead, the patient-specific virtual boundary (PS-VB) can be generated in parallel, while the generic virtual boundary (G-VB) remains in its original form. After the patient-specific virtual boundary (PS-VB) is generated, the generic virtual boundary (G-VB) can be replaced by the same. Alternatively, the generic virtual boundary (G-VB) can be gradually morphed into the patient-specific virtual boundary (PS-VB) such that the generic virtual boundary (G-VB) gradually changes shape from its original form.

The patient-specific virtual boundary (PS-VB) and anatomical model (AM) can be registered to the physical anatomy (A) using any suitable registration technique, such as touching on the anatomy with the pointer P, imaging registration, machine vision registration, or any other type of technique. The navigation system 32 can track the anatomy (A) and the surgical tool 20 using any tracking technique described herein, or otherwise. With the registered patient-specific virtual boundary (PS-VB), the system 10 can perform patient-tailored operations for controlling the tool 20. For example, the system 10 can constrain the tool 20 from extending beyond the patient-specific virtual boundary (PS-VB).

For illustrative purposes, the features are also described and shown for a partial knee arthroplasty for a tibial distal case. Of course, the techniques described herein may be utilized for anatomical resections other than those shown herein.

Any of the techniques described herein can be implemented by components or controllers 30 of surgical system 10 and/or by the software program 80 executed by the surgical system 10. The software program 80 may be embodied by the clinical application 74 and/or the controller 30, or any part thereof. Steps of the computer-implemented method of executing these techniques can be understood from the description below.

A. Geometric Engine

The geometric engine 72 is configured to compute and/or execute geometric operations that are needed to produce the patient-specific virtual boundary (PS-VB), or any part thereof. The inputs into the geometric engine 72 include the anatomical model (AM) of the anatomical volume (A) and the generic virtual boundary (G-VB). As described below, the generic virtual boundary (G-VB) can be derived from various sources. The geometric engine 72 is further configured to geometrically morph the generic virtual boundary (G-VB) into the patient-specific virtual boundary (PS-VB).

The geometric engine 72 comprises a geometric modelling kernel, which is a 3D solid modeling software component. One example of such a modelling kernel is Parasolid. The geometric engine 72 can output the patient-specific virtual boundary (PS-VB). Optionally, the path generator 68 can subsequently produce the milling path, based in part, on the results or output of the geometric engine 72 relating to the generation of the patient-specific virtual boundary (PS-VB). A milling path is not always required.

The anatomical model (AM) inputted into the geometric engine 72 can be 3D virtual model of the anatomical volume (A), e.g., a bone, such as the femur, tibia, hip, etc. The anatomical model (AM) may be defined as a CAD model, open or closed mesh or any other volumetric image representation. In one example, the bone model is a mesh that is converted into a CAD solid body model. The anatomical model (AM) may be generated in any file format, such as STL (Stereo Lithography) or VRML (Virtual Reality Modeling Language). The mesh may be derived from pre-operative imaging of the anatomical volume (A). The imaging modalities may be any one or more of CT, MRT, X-ray, Fluoro, MRI, and the like. These imaging modalities output slices that can be converted into the anatomical model (AM) through a process called segmentation. In other examples, the anatomical model (AM) can be generating without imaging. Instead, a pointer tracked by the navigation system 32 can be touch to the surface of the anatomical volume (V) to create a point cloud from which the anatomical model (AM) can be derived. The anatomical model (AM) may be generated using any technique other than those described herein. The anatomical model (AM) could be one or more surfaces and does not need to be a complete bone or tissue model. Moreover, segmentation is not required to generate the anatomical model (AM).

The geometric engine 72 is configured to enable loading, storing, manipulating, and/or creating the anatomical model (AM). The geometric engine 72 may do so with or without visualization on the display 38. The geometric engine 72 can also convert between all 3D representations utilized for the anatomical model (AM), thereby providing multimodal 3D model representation.

The geometric engine 72 can compute intersections between the anatomical model (AM) and other objects, such as the generic virtual boundary (G-VB), patient-specific virtual boundary (PS-VB), implant models (IM), allowed volumes (AV), etc.

Another feature of the geometric engine 72 is the ability to perform planar, non-planar or 3D offset operations. For example, offset operations can define a surface that is spaced apart from another surface by a predefined distance. One output of the offset operation is to offset the patient-specific virtual boundary (PS-VB) from the feature of the anatomical model (AM), which is described below. As will be understood further below, the geometric engine 72 can also perform sweeps or extruding operations to generate offset geometry.

Furthermore, the geometric engine 72 is configured to represent curves, such as polygons and spline curves. One example output of such features is generation of the intersection contour, described herein. In addition, the geometric engine 72 can convert and/or approximate freeform curves into polygons, and vice versa. For example, this feature is helpful to facilitate forming of freeform implants or bone removal volumes.

Through these features and capabilities, the geometric engine 72 enables a patient-specific on-the-fly (intraoperative and near-real time) autonomous generation of the patient-specific virtual boundary (PS-VB), even for freeform implants that are intraoperatively defined by the surgeon. Additional capabilities of the geometric engine 72 will be understood from the description to follow. The geometric engine 72 may comprise features and capabilities other than those specifically described herein.

Any functionality described herein that is attributed to the geometric engine 72 may also be attributed to the boundary generator 66 and/or path generator 68 and/or software program 80 generally. For example, the boundary generator 66 may have responsibility of generating in part, or in whole, the generic virtual boundary (G-VB) and/or patient-specific virtual boundary (PS-VB). The path generator 68 might have overall responsibility for the process of creating milling path. The boundary and path generators 66, 68 can make sub-calls to the geometric engine 72 for performing various geometric operations during the process.

B. Generic Virtual Boundary

The generic virtual boundary (G-VB) is a customizable geometrical object that is configured to provide a virtual constraint on the tool 20. The generic virtual boundary (G-VB) is designed to keep the tool 20 inside a workspace, or keep the tool 20 outside a workspace. In one example, the generic virtual boundary (G-VB) separates regions where the tool 20 is allowed to move from regions where the tool 20 is prohibited from moving. To this end, the generic virtual boundary (G-VB) comprises one or more surfaces that define the "walls" of the virtual boundary. In this way, the generic virtual boundary (G-VB) is distinguished from other types of known constraints, such as tool path constraints, and the like.

When the tool 20, e.g., TCP of the tool 20, interacts with the virtual boundary, the system is designed to simulate reactive force to slow-down or push back the tool 20 away from the wall. Examples of how virtual boundaries are utilized to constrain a tool are described in U.S. patent application Ser. No. 16/000,498, entitled "Robotic Surgical System And Method For Producing Reactive Forces To Implement Virtual Boundaries," Filed Jun. 14, 2018, the disclosure of which is incorporated by reference in its entirety.

The generic virtual boundary (G-VB) is not patient-specific, but rather, patient-generic and may be designed for the "ideal patient" using worst-case scenario parameters.

The generic virtual boundary (G-VB) is inputted into the software program 80, and more specifically, the geometric engine 72 and the boundary generator 66.

As will be described, the generic virtual boundary (G-VB) is customizable using the morphing techniques described herein. That is, the generic virtual boundary (G-VB) is customizable into the patient-specific virtual boundary (PS-VB). The generic virtual boundary (G-VB) may comprise specialized faces that are morphable and other faces that are non-morphable. In one example, the generic virtual boundary (G-VB) is morphed into the patient-specific virtual boundary (PS-VB) based on the specific patient anatomy (bone) so that the patient-specific virtual boundary (PS-VB) can meet milling requirements, i.e., so that the resulting size of the patient-specific virtual boundary (PS-VB) is precisely tailored to the anatomy (not too large or too small). However, the patient-specific virtual boundary (PS-VB) can be generated for purposes unrelated to milling, e.g., such as generally constraining tool 20 movement.

The generic virtual boundary (G-VB) may also comprise or be associated with a reference surface (E) that is sized or sizable to intersect a cross-section of the entire bone. The reference surface (E) may be planar or non-planar. The reference surface (E) is described below.

Figure 4:
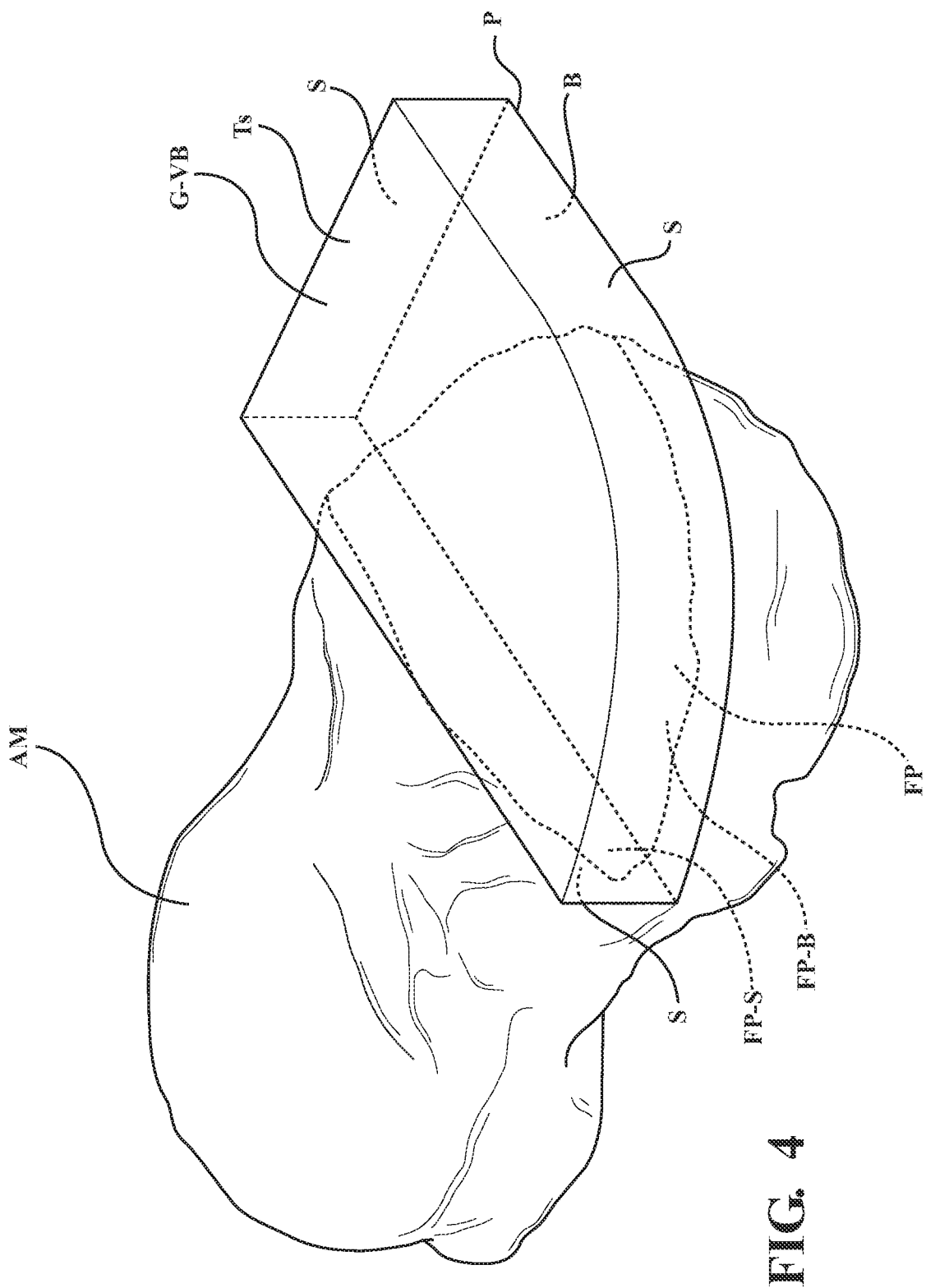
FIG. 4 illustrates a generic virtual boundary positioned with respect to an anatomical model of the tibia.

Based on the volumetric intersection of the anatomical model (AM) and the generic virtual boundary (G-VB), a footprint (FP) can be defined, as shown in FIG. 4. The footprint (FP) comprises one or more contact or mating surfaces between the anatomical model (AM) and the generic virtual boundary (G-VB). These contact surfaces may or may not be associated with the implant model (IM). The footprint (FP) is derived from geometric features of the generic virtual boundary (G-VB). In this example, the footprint (FP) comprises a base footprint surface (FP-B) and adjacent side footprint surfaces (FP-S). However, the footprint (FP) may comprise any combination of lower, upper, or side contact surface. The footprint (FP) may be planar or non-planar and may take any primitive or complex shape depending on the simplicity of the generic virtual boundary (G-VB). The footprint (FP) can be identified by the software program 80 for purposes of morphing the generic virtual boundary (G-VB) according to the techniques described herein.

The geometric engine 72 may comprise an algorithm for defining the footprint (FP). The algorithm may generate the footprint (FP) using interpolation, least squares approximation, and/or shape approximations derived from the geometry of the implant model (IM). Hence, the footprint (FP) may be freeform surface or a CAD modeled surface. Further examples and uses of the generic virtual boundary (G-VB) are described below.

1. Examples of Generic Virtual Boundaries

The generic virtual boundary (G-VB) may be generated in various ways, from various sources, and to provide various functionality. For any variation of the generic virtual boundary (G-VB) specifically described herein or not, the techniques described herein are capable of morphing the generic virtual boundary (G-VB) into the patient-specific virtual boundary (PS-VB).

a. Generic Virtual Boundary Based on Implant Model

Figure 3:
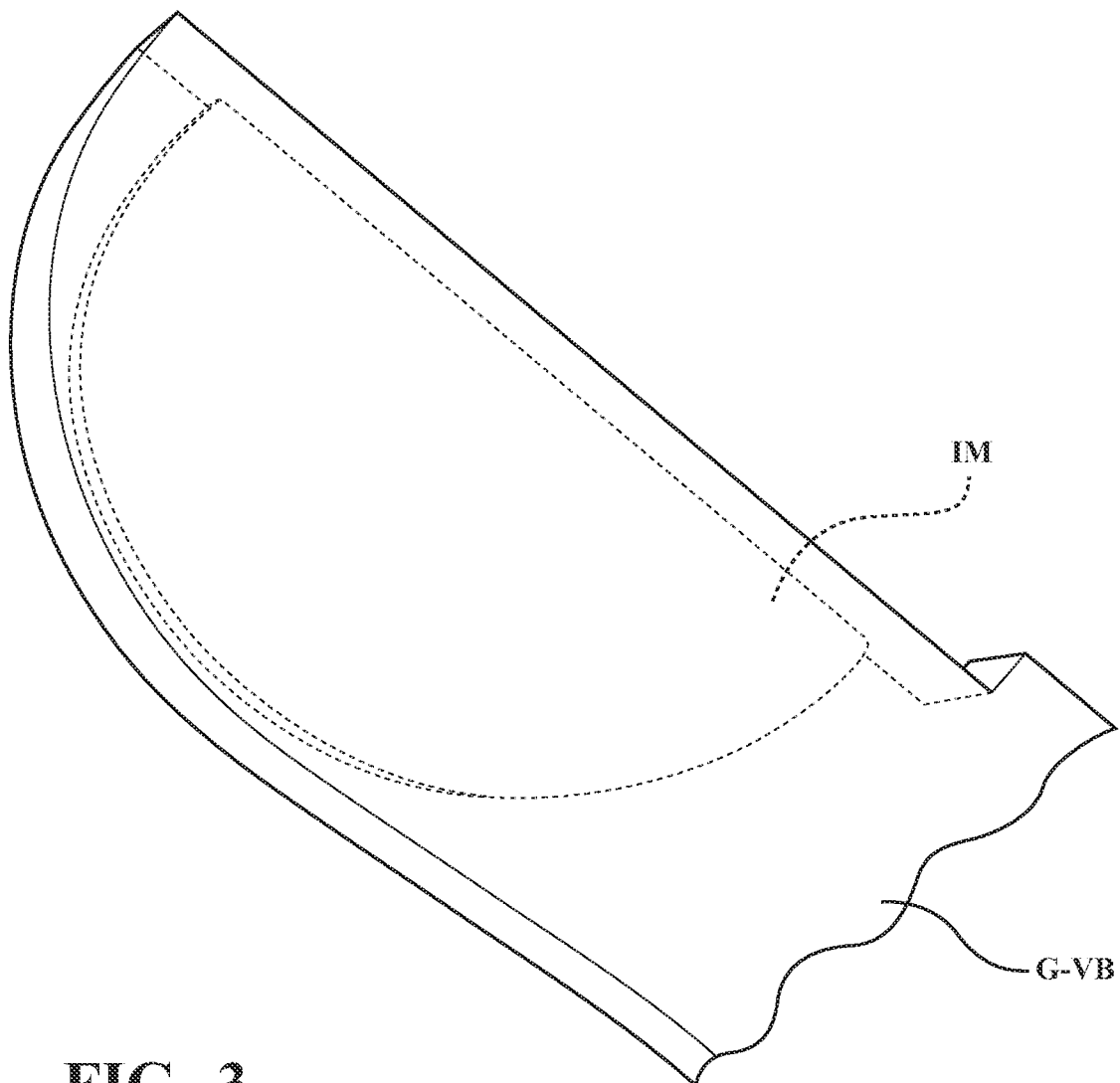
FIG. 3 is one example of an implant model for distal tibial arthroplasty with a generic virtual boundary associated therewith.

The generic virtual boundary (G-VB) can be based on an implant model (IM), as shown in FIG. 3. The implant model (IM) is a virtual 3D model of the physical implant that is intended for implantation into the anatomical volume (A). These models may be represented as 3D CAD solid bodies. The implant model (IM) may be any surgical implants, such as partial knee implants, including unicompartmental, bicompartmental, multicompartmental, total knee implants, spinal implants, hip implants, or the like.

The implant model (IM) can be selected from or otherwise derived from an electronic catalog of predefined implant models (IM). The generic virtual boundary (G-VB) can be defined along the implant model (IM) and positioned with the implant model (IM). Alternatively, the generic virtual boundary (G-VB) can be generated from the implant model (IM). The generic virtual boundary (G-VB) may comprise a corresponding constraint template that is also implant specific.

Implant selection is made such that the corresponding implant model (IM) generically fits to the corresponding anatomical model (AM) in the region of implantation. Implant type and implant size selection is either made by and/or approved by the surgeon performing the procedure. This selection could be made pre-operatively and imported at the beginning of the procedure, and/or modified intra-operatively using the clinical application 74 shown on the displays 38 and by using one or more of the input devices 40, 42. The implant model (IM) could hold an entire plan or factors of the surgical plan.

Additionally or alternatively, the implant model (IM) may be defined 'free-form' or 'drawn on-the-fly by the surgeon'. The implant model (IM) can be drawn, modeled, or adjusted by the surgeon using the input devices 40, 42 of the navigation system 32. In particular for these examples, the implant model (IM) may not necessarily represent a physical component to be installed into the bone, but rather represents a 'negative' of the desired bone/tissue to be removed. For such non-implant examples, it is also possible the 'non-implant' bone volume/shape to be removed comes from a pre-defined database or catalog, or calculated/suggested by the software or by a vendor-provided pre-operative plan. Hence, the 'non-implant' case is not limited to free-form or drawn on-the-fly examples.

In other applications, bone/tissue resection is being performed, but not necessarily for the primary purpose of receiving an implant. For this case, the implant model (IM) could be replaced with a solid model representative of the 'negative' of the bone/tissue to be removed. This solid model can be inputted into the geometric engine 72. Hence, the generic virtual boundary (G-VB) can be generated from a resection target.

The geometric engine 72 is configured to enable loading, storing, manipulating, and/or creating the implant model (AM). The geometric engine 72 may do so with or without visualization on the display 38.

The software program 80, with assistance from the geometric engine 72, is configured to compute geometric interactions between the anatomical model (AM) and the implant model (IM).

b. Generic Virtual Boundary Defined Manually and/or On-The-Fly

In another example, the generic virtual boundary (G-VB) is derived from input by the surgeon. By virtue of the capabilities of the geometric engine 72, it is possible to generate the generic virtual boundary (G-VB) intraoperatively or on-the-fly. For example, the surgeon may decide to intraoperatively change a preoperatively-selected generic virtual boundary (G-VB). The surgeon can also select one of a plurality of different generic virtual boundaries (G-VB). Alternatively, the surgeon may manually define the generic virtual boundary (G-VB) partially or entirely by virtually defining and positioning geometrical primitives and shapes. Further techniques for generating virtual boundaries can be like those described in U.S. patent application Ser. No. 15/952,810, filed Apr. 13, 2018, entitled, Surgical Systems and Methods for Facilitating Ad-Hoc Intraoperative Planning of Surgical Procedures, the disclosure of which is hereby incorporated by reference in its entirety.

In either instance, the surgeon can create or modify any solid body for defining the generic virtual boundary (G-VB). For example, the surgeon can use the input devices 40, 42 of the navigation system 32 to define parameters or landmarks for definition of the generic virtual boundary (G-VB). For example, the surgeon may define the generic virtual boundary (G-VB), partially or entirely, free-hand using the input devices 40, 42. Additionally or alternatively, the pointer P can be utilized for selecting or tracing the boundaries of the bone/tissue regions to be removed. The software program 80 can access the navigation data from the navigation system 32 and the geometric engine 72 can analyze the data and synthesize the generic virtual boundary (G-VB). Such techniques can be utilized whether or not the generic virtual boundary (G-VB) is based on the implant model (IM).

Additionally or alternatively, the generic virtual boundary (G-VB) can be defined using any predefined solid bodies, primitive volumes, or any mathematically described surface or volume not described herein.

The generic virtual boundary (G-VB) can be defined based on a surgeon's preference to include a certain distance of interference or clearance between the implant and preparation surface.

In other examples, the generic virtual boundary (G-VB) can be automatically defined. For example, interference fit can be tailored based on a patient anatomical parameter such as bone density and/or elastic modulus for consistent effective interference fit, such as described in U.S. Patent Application Publication No. 20150080717A1, the disclosure of which is incorporated by reference in its entirety.

c. Generic Virtual Boundary Defined by or with Allowed Volume

Figure 5:
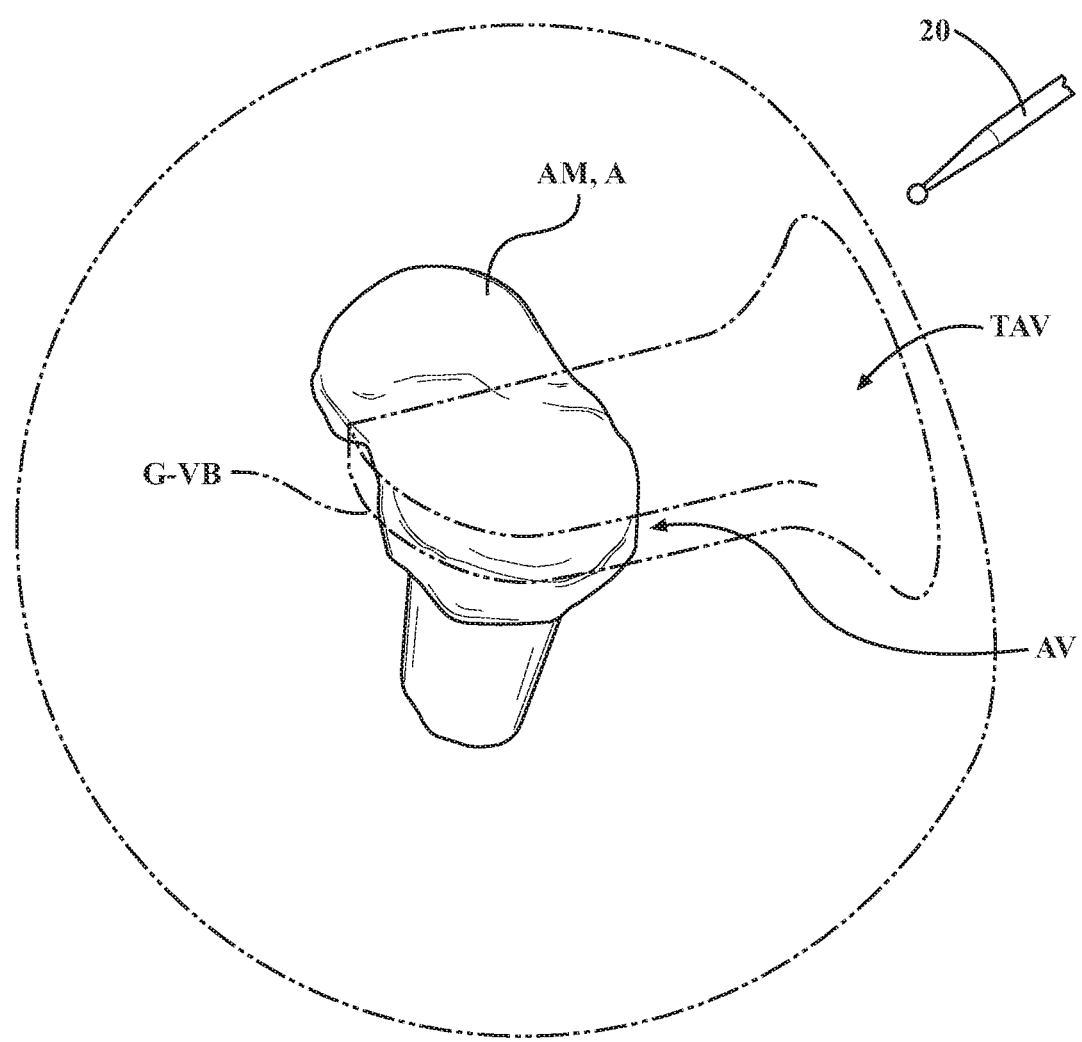
FIG. 5 illustrates the generic virtual boundary as a component of a greater allowed volume for constraining a surgical tool.

According to one example, the generic virtual boundary (G-VB) is at least partially derived from, based on, or associated with an allowed volume (AV), as shown in FIG. 5. The allowed volume (AV) at least partially intersects the anatomical volume (A). Typically, the allowed volume (AV) is a generic volume.

The allowed volume (AV) is the region where milling is potentially allowed. The allowed volume (AV) is a subset of (often less than, but at a maximum being equal in volume to) the region where the tool 20 is allowed to move. The allowed volume (AV) is potentially more restrictive than the region where the tool 20 is allowed to move. In order to mill, the tool 20 must be able to move. However, in order to move, the tool 20 does not need to be able to mill. The less restrictive region where the tool 20 is able to move is important to allow the user to move the tool 20 in and out of the surgical site during the procedure, for example, to get the tool 20 out of the way in order to clean up soft tissue, apply suction, inspect the anatomy, etc.

In some instances, the generic virtual boundary (G-VB) or the allowed volume (AV) may be understood as a "keep in" volume, in terms of movement of the tool 20 during milling. The virtual boundaries are often "keep out" boundaries. Any combination of keep-in and/or keep-out virtual boundaries may be mixed along with a keep-in allowed volume (AV) since the allowed volume (AV) part is used for the autonomous milling path generation.

The allowed volume (AV) may be associated with the implant model (IM) designed for insertion into the anatomical volume (A). In some examples, each implant model (IM) in the electronic catalog may comprise a corresponding and customized allowed volume (AV).

For the implant-specific virtual boundary case, the allowed volume (AV) can be defined (manually) offline as part of a CAD model for each implant size. The allowed volume (AV) could be input data for the system 10, used by the clinical application 74 and passed into the geometric engine 72 at runtime. The allowed volume (AV) can also be generated intraoperatively or on-the-fly.

The allowed volume (AV) further comprises a tool access volume (TAV), as shown in FIG. 5. The tool access volume (TAV) may be seamlessly integrated with the generic virtual boundary (G-VB) and is configured to guide the tool 20 to the anatomical volume (A). The tool access volume (TAV) may be any suitable geometry, such as an access funnel, cone, bubble, hemi-sphere, prism, or the like. The tool access volume (TAV) entry guides the user into the zone of the generic virtual boundary (G-VB). This is done because the tool access volume (TAV) and allowed volume (AV) are used in part to define the virtual boundary that the user cannot pass through in manual mode, as they are leading the tool 20 into the surgical site. If the user hits the entry of the tool access volume (TAV), the tool 20 is smoothly deflected off the virtual boundary and the tool 20 is guided towards the surgical site. Once inside the tool access volume (TAV) or allowed volume (AV), the user can start the energy applicator and enable autonomous milling.

Examples of generic virtual boundaries (G-VB) other than those described herein are fully contemplated and can be subject to the patient-specific morphing techniques described herein.

C. Patient-Specific Virtual Boundary

With reference to FIGS. 6-12, this section describes details to further enable morphing of the generic virtual boundary (G-VB) to a surface feature of the anatomical model (AM) to generate the patient-specific virtual boundary (PS-VB).

Morphing may be executed according to techniques other than those specifically described herein. Furthermore, the examples herein focus on morphing the generic virtual boundary (G-VB) for the tibia as the anatomical volume (A). Of course, the generic virtual boundary (G-VB) can be morphed for any anatomical volume (A).

The system 10, controllers 30, software program 80 and geometric engine 72 can carry out, individually, and in combination, various computer-implemented functions for preparing and executing morphing, including but not limited to, functions for: converting mesh to CAD bodies, or vice-versa; intersecting and subtracting curves, surfaces, sheet and solid bodies; spline fitting to convert polygons into spline curves; mapping to define relations between original and morphed edges and faces; spline surface creation; replacing surfaces of faces; sweeping along a curve; generating offsets; linear extrusion; sewing or merging faces; and the like. These various functions will be understood in the context of the description herein. Moreover, the steps described herein can be carried out in any suitable order other than the order described herein.

Initially, the mesh of the anatomical model (AM) may need to be converted to a CAD solid body model to be compatible for morphing processing. This step can be performed offline and may not be required depending on the input source of the anatomical model (AM).

The generic virtual boundary (G-VB) is provided by the system 10, according to any manner described. In the example of FIG. 4, the generic virtual boundary (G-VB) is associated with, based on, or otherwise derived from an implant model (IM) and positioned for a multi-compartmental tibial distal resection. With reference to FIG. 4, the generic virtual boundary (G-VB) for this specific tibial application comprises a base (B) and adjoining side surfaces (S). In this example, the base (B) is planar. The base (B) has a perimeter (P) and the side surfaces (S) are arranged transverse, and more specifically, orthogonal to the base (B) and along the base perimeter (P). The generic virtual boundary (G-VB) can also include a top surface (Ts) opposite the base (B). Of course, depending on the scenario, the generic virtual boundary (G-VB) can have any geometry other than that shown in FIG. 4. The surfaces of the generic virtual boundary (G-VB) can be planar or curved. The generic virtual boundary (G-VB) can also include any number of layers and can be an open or closed geometry.

Any of these surfaces, perimeters, or edges, or other geometrical features of the generic virtual boundary (G-VB) is configured to be morphed. Additionally, there may be features of the generic virtual boundary (G-VB) that are non-morphable.

The generic virtual boundary (G-VB) is positioned proximate to the anatomical model (AM). Positioning of the generic virtual boundary (G-VB) can be executed or visualized using the GUI 96 displayed on any of the displays 38 of the system 10. The user may manually position generic virtual boundary (G-VB) proximate to the anatomical model (AM). Input from any of the input devices 40, 42 can be utilized to facilitate such positioning. Alternatively, the software program 80 may automatically position the generic virtual boundary (G-VB) proximate to the anatomical model (AM). The program 80 can utilize a best-fit algorithm or default placement of the generic virtual boundary (G-VB) based on preset parameters or distances.

In one example, positioning the generic virtual boundary (G-VB) occurs preoperatively, i.e., according to a preoperative plan. Alternatively, and advantageously, positioning the generic virtual boundary (G-VB) may occur intraoperatively. If the surgeon is not satisfied with the pre-operative plan, or if unforeseen circumstances arise, the surgeon can freely update the positioning the generic virtual boundary (G-VB) intraoperatively. By use of the techniques described herein, the system can perform the aforementioned morphing on-the fly, without requiring significant delays for computational time. An updated patient-specific plan, including an updated virtual boundary, and optionally a resection volume and milling path, can quickly be generated intraoperatively.

Figure 6:
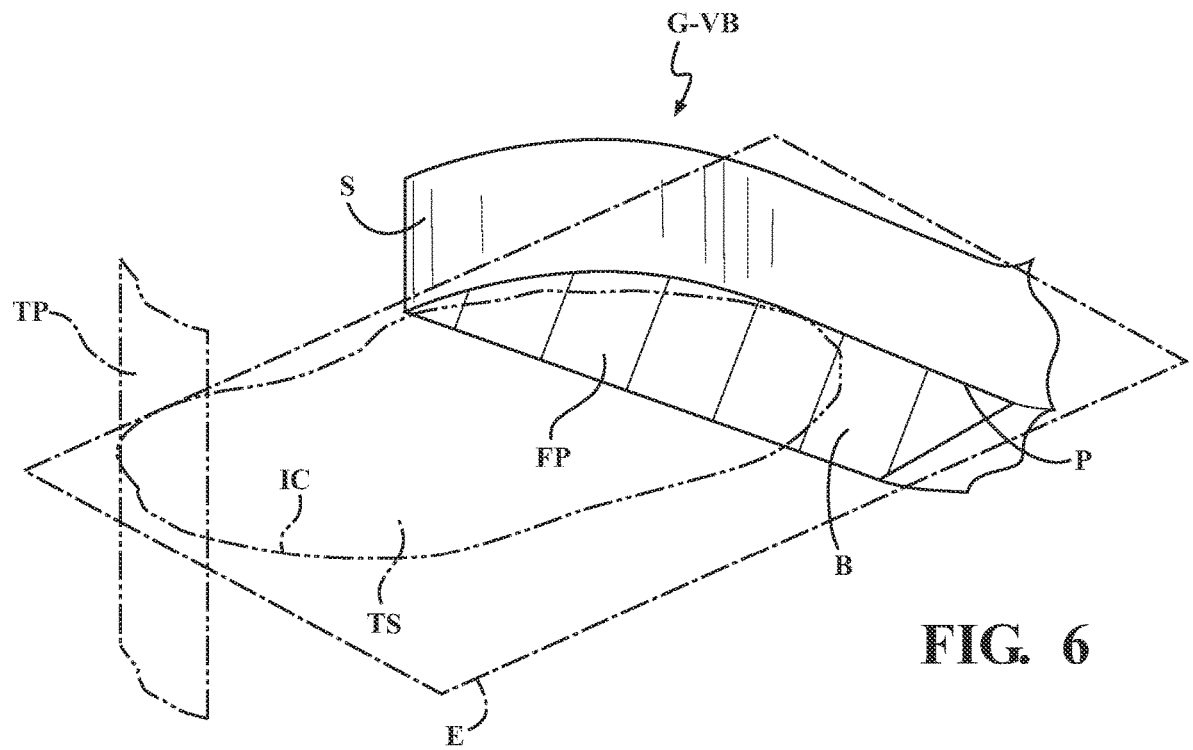
FIG. 6 illustrates definition of a cross-sectional contour of the anatomical model with respect to the generic virtual boundary in furtherance of defining the patient-specific virtual boundary.

Referring to FIG. 6, a patient-specific function is carried out wherein the anatomical model (AM) is intersected with a reference surface (E) that is sized or sizable to intersect a cross-section encompassing, in part, or in whole, the perimeter of the anatomical model (AM). The reference surface (E) may be finite or infinite in size. In this example, the reference surface (E) is planar, but may also be non-planar, a freeform surface or may comprise several planar strips. In this example, the reference surface (E) encompasses the base (B) of the generic virtual boundary (G-VB) as well as the base footprint (FP) surface, which are co-planar to each other.

For this example, the result of this intersection between the reference surface (E) and the anatomical model (AM) is an intersection contour (IC) that is a closed geometry. However, the intersection contour (IC) may be an open geometry depending on the application, reference surface (E), and anatomical model (AM). Here, the intersection contour (IC) is a cross-sectional perimeter of the anatomical model (AM) sliced by the reference surface (E) plane. The intersection contour (IC) is patient-specific because its geometry is derived specifically from the patient's anatomical model (AM). The intersection contour (IC) can be defined using techniques other than using the reference surface (E). For instance, the intersection contour (IC) can be defined based on the intersection of one or more surfaces generic virtual boundary (G-VB) with the anatomical model (AM). In FIG. 4, for example, the base surface (B) of the generic virtual boundary (G-VB) can be utilized to identify the intersection contour (IC).

The intersection contour (IC) is utilized, in whole, or in part, to define foundational parameters of the patient-specific virtual boundary (PS-VB). In the examples described herein, only the part of the intersection contour (IC) that overlaps the generic virtual boundary (G-VB) is considered. Specifically, the intersection contour (IC) is considered for morphing only for those portion of the intersection contour (IC) that require patient-specific morphing to prevent the tool 20 from contacting adjacent soft tissue regions of the anatomy. Alternatively, the entire intersection contour (IC) may be considered. The geometric engine 72 may define the intersection contour (IC) as a polyline or spline curve. In one example, the intersection contour (IC) is a planar polygon which is approximated by a planar (least square) fitting spline.

The intersection contour (IC) is coincident to the reference surface (E). According to one technique, the intersection contour (IC) is created by using the reference surface (E). In one example, the intersection contour (IC) can be geometrically trimmed from the reference surface (E) by intersection. The geometric engine 72, for example, may trim regions of the reference surface (E) that are outside of the intersection contour (IC), while preserving a region within the intersection contour (IC). Trimming of the reference surface (E) can be in a direction along a trimming (section) plane (TP) that is orthogonal to the reference surface (E). The geometric engine 72 can be used to determine a portion (TS) of the reference surface (E) which is inside of the intersection contour (IC). This portion is a trimmed surface (TS), which can also be understood as a face, bounded by the intersection contour (IC) and coincident to the reference surface (E). As will be described below, the system 10 may utilize the trimmed off regions of the reference surface (E) to later provide a geometric foundation to virtually define offsets for the patient-specific virtual boundary (PS-VB).

While trimming is described above as one way of defining and extending a surface, the system 10 may utilize any other computer-implemented technique for doing the same. For example, the intersection contour (IC) and corresponding surface may be altered from its original geometry in a planar direction using geometric functions. Moreover, while the reference surface (E) is described above, there may be various ways to provide a similar result.

Here, the side surface (S) and base (B) surface of the generic virtual boundary (G-VB) are configured to morph. As used herein, the side surface (S) can be one surface or a side surface region that is a collection of many individual side surfaces. The surfaces may be the same or different type. As such, the side surface (S) can alternatively be referred to as a side surface region. The perimeter (P) of the generic virtual boundary (G-VB), along which the side surface (S) is disposed, is also configured to morph. The subsequent description focuses on the side surface (S) because of the significance the effect the virtual boundary associated with the side surface (S) has on milling the tibia for onlay implants. Namely, if the side surface (S) is not truly patient-specific, there may be undercutting or overcutting at the perimeter edge of the tibia. Notably, these techniques below can be utilized to morph any other surface of the generic virtual boundary (G-VB) and the description is not limited solely to side surfaces.

The following sections describe variations of the patient-specific virtual (PS-VB) that build upon the introductory features of the patient-specific morphing techniques described above. These variations are a non-offset patient-specific virtual (PS-VB) and an offset patient-specific virtual (PS-VB').

1. Non-Offset Version of Patient-Specific Virtual Boundary

This section describes an example of the patient-specific virtual boundary (PS-VB) that is morphed to the anatomical model (AM) but is not offset.

Figure 7:
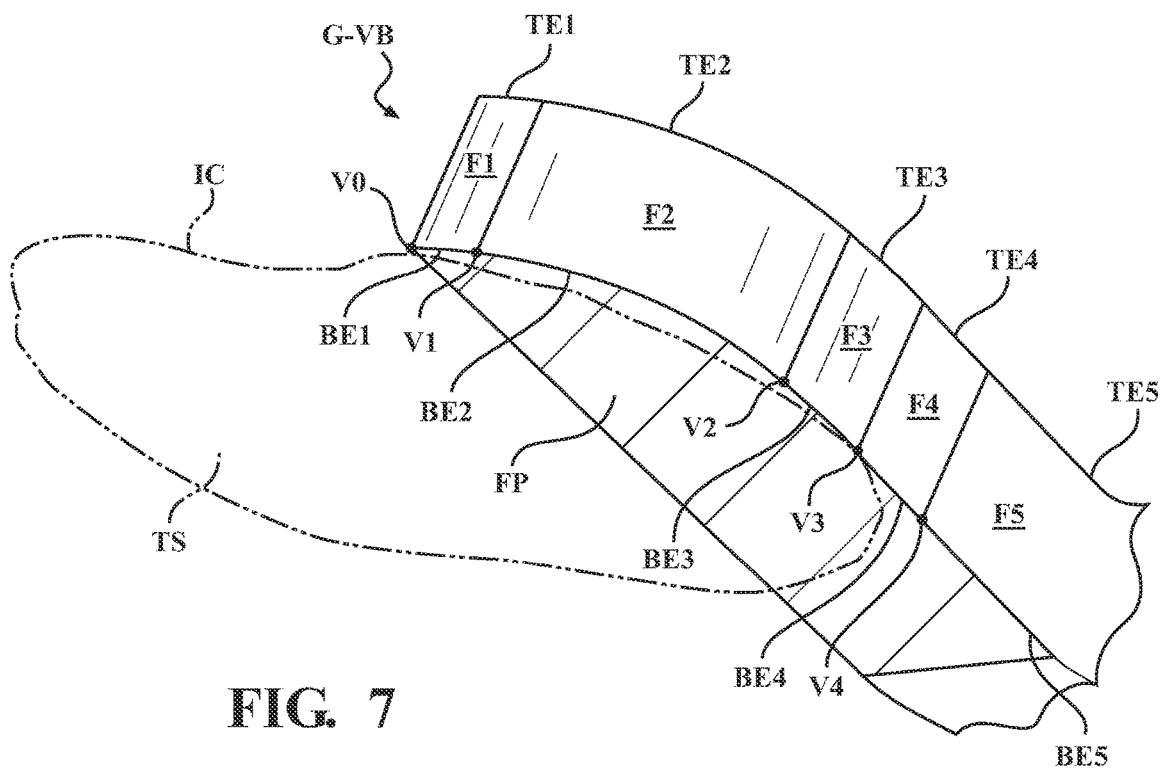
FIG. 7 is the view of FIG. 6 further utilizing the cross-sectional contour to define faces of the generic virtual boundary that will be morphed according to the techniques described herein.

Referring to FIG. 7, the software program 80 utilizes the intersection contour (IC) from FIG. 6. To identify how to morph the generic virtual boundary (G-VB) given the intersection contour (IC), the software program 80 collects candidate morphable faces (F). More specifically, for this example, the side surface (S) is broken down into a plurality of candidate morphable side faces (F). Alternatively, the side surface (S) is broken down into a plurality of candidate morphable side surfaces, rather than faces. As used herein, a face is a bounded portion of a surface. A face may be bounded by loops, where each loop is a closed ordered set of edges. Normally every face is a subset of a surface. However, the term faces and surfaces can be interchanged for any use herein.

The software program 80 identifies the geometrical relationship between the side surface (S) and the anatomical model (AM). In the described example, the software program 80 utilizes a planar approach to determine morphable and non-morphable edges through analysis of the intersection contour (IC) relative to the side surface (S) edges. However, the software program 80 may utilize a 3D approach wherein the software program 80 determines morphable and non-morphable surface areas through analysis of the anatomical model (AM) volume relative to the side surface (S).

For tibial examples, the software program 80 can identify the geometrical relationship between the side surface (S) and the trimmed surface/face (TS) for determining how to define the morphable side faces (F).

This determination can be performed in various manners. In one example, the software program 80 identifies edges of the side surface (S) that are disjoint or not co-planar with the trimmed surface/face (TS). The software program 80 can make this determination with respect to a plane that is orthogonal to the side surface (S), such as the reference surface (E). In this example, top edges (TE) of the side surface (S) are not co-planar with the trimmed surface/face (TS). The software program 80 may also evaluate the distance of an edge to the resection anatomical model (AM) to determine if an edge should be morphed.

Each top edge (TE) can be utilized to delineate a potential morphable face (F). The top edges (TE) in this example will not be morphed because they are above the anatomical model (AM) and hence virtual boundaries associated therewith will not affect milling. There may be any number of top edges (TE). The top edges (TE) can be split into any number of sub-edges.

Each top edge (TE) has a corresponding bottom edge (BE). For simplification, we assume in this example that each morphable face (F) has only one top edge (TE) and one corresponding bottom edge (BE). However, each morphable face (F) may have more than one top edge (TE) and bottom edge (BE). The bottom edge (BE) and corresponding top edge (TE) have the same length, however, they may have different lengths.

The geometric engine 72 can breakdown the side surface (S) into any number of morphable side faces (F). In this example, four morphable side faces (F1-F4) are defined, each having a corresponding top edge (TE1-TE4) and bottom edge (BE1-BE4). Side face (F5) is not morphable, but is rather fixed, for reasons that will be apparent below.

The software program 80 may define any number of morphable faces (F) and may do so in any suitable way and based on any appropriate consideration, such as the geometry of the intersection contour (IC), geometry of the generic virtual boundary (G-VB), computational time and efficiency, cost functions, and the like.

In one example, the side surface (S) or any morphable side face (F) can be split where there is an intersection point between the trimmed surface/face (TS) and the side surface (S). For example, at vertex (V3) in FIG. 6, the intersection contour (IC) intersects the side surface (S). A plane through this intersection point and orthogonal to the edge tangent at this point can be generated to delineate side faces (F3) and (F4), and their respective edges. In this example, vertex (V3) is the lower left vertex of the last morphable face (F4) of the patient-specific virtual boundary (PS-VB) and provides a transition between morphable and non-morphable portions of the patient-specific virtual boundary (PS-VB). However, the transition between morphable and non-morphable portions can be delineated based on any other geometrical condition. Such transitions are described further below.

The bottom edges (BE) in this example will be morphed to the intersection contour (IC) because these bottom edges (BE) are proximate to or may collide with the bone boundary and hence virtual boundaries associated therewith will affect milling. These edges are referred to as morphable edges. Once the morphable edges are defined, one or more vertices (V) are defined at the start and end points of each morphable edge. Here, morphable edges are geometric features that represent a bounded piece of a single curve. The vertices (V) can be arranged as an ordered list, wherein bottom edge (BE1) is defined between vertices (V0) and (V1), bottom edge (BE2) is defined between vertices (V1) and (V2), and so on. Any number of vertices (V) may be defined based on the number of morphable edges. Moreover, while the bottom edge (BE) is morphable in this example, any other edge can be morphed.

Figure 8:
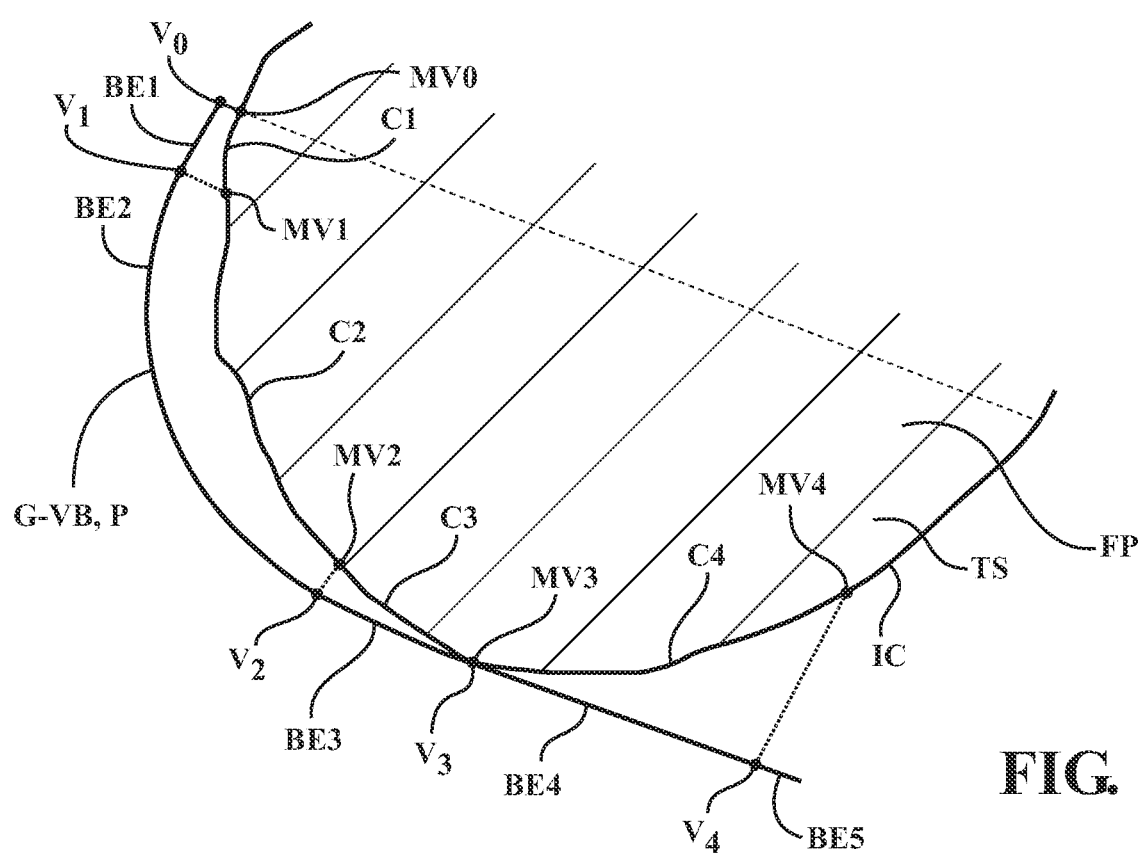
FIG. 8 is a top down view of the generic virtual boundary and a portion of the cross-sectional contour of FIG. 7.

With reference to FIG. 8, a top down view from FIG. 7 is provided showing the planar geometric relationship between the morphable bottom edges (BE1-BE4) and the intersection contour (IC). Using the defined vertices (V), a patient-specific mapping function is executed by the software program 80 to define a relationship between the generic virtual boundary (G-VB) and the anatomical model (AM). More specifically, for the tibial example, the software program 80 maps a relationship between the bottom edges (BE) of corresponding side faces (F) and the intersection contour (IC) in furtherance of generating morphed faces or surfaces of the patient-specific virtual boundary (PS-VB).

The vertices (V) on the generic virtual boundary (G-VB) are mapped to the intersection contour (IC). For each vertex (V) the program 80 defines a normal plane to its corresponding/related bottom edge (BE) at (V). The closest intersection point of the normal plane and the intersection contour (IC) is identified by the program 80. These intersection points are called morphed vertices (MV). In one example, a bottom edge (BE) is entirely morphable when its vertices (V) produce two corresponding morphed vertices (MV) when mapped. For example, vertices (V0 and V1) of (BE1) produce two morphed vertices, (MV0) and (MV1), vertices (V1 and V2) of (BE2) produce two morphed vertices, (MV1) and (MV2), and so on. For this reason, bottom edges (BE1-BE4) are each morphable since their respective vertices (V) produce two corresponding morphed vertices (MV). However, in FIGS. 7 and 8, bottom edge (BE5) is non-morphable or only partially morphable by the software program 80. Mainly, although vertex (V4) produces one morphed vertex (MV4) when mapped, there will be no other morphed vertex (e.g., MV5). In other words, a plane normal to bottom edge (BE5) from the other end of the bottom edge (BE5) will not intersect the intersection contour (IC). Such edges can provide transitions between morphed and non-morphed faces or surfaces, as will be described below.

Again, although this mapping function has been explained in a 2D context (i.e., between bottom edges (BE) of the side surface (S) and the intersection contour (IC)), the software program 80 may utilize any 3D mapping, such as mapping points, lines or areas on the side surface (S) to the surface of the anatomical model (AM), etc.

Moreover, the above example is one way to determine whether or not geometry of the generic virtual boundary (G-VB) should be morphable. Other examples are fully contemplated for doing the same, such as projecting contours or surfaces of the anatomical model (AM) onto a contour or surface of the generic virtual boundary (G-VB), or the like.

Referring back to FIG. 8, the morphed vertices (MV) are utilized to define morphable segments (C) that are coincident to the intersection contour (CV). Each segment (C) is a curve along the intersection contour (IC) bound by two adjacent morphed vertices (MV). In the example of FIG. 8, segment (C1) is bound by morphed vertices (MV0) and (MV1), segment (C2) is bound by morphed vertices (MV1) and (MV2), and so on. In FIG. 8, the result of this process is four morphable segments (C1)-(C4). Each segment (C1)-(C4) is derived from a corresponding bottom edge (BE1)-(BE4) by the mapping function. These segments (C1)-(C4) match the intersection contour and replace the bottom edges (BE1)-(BE4).

Notably, there is no morphable segment (e.g., C5) in this example because there exists no morphed vertex (MV5) to bind such. Such segments will enable transitions between morphable and non-morphable portions of the generic-virtual boundary (G-VB).

Figure 9:
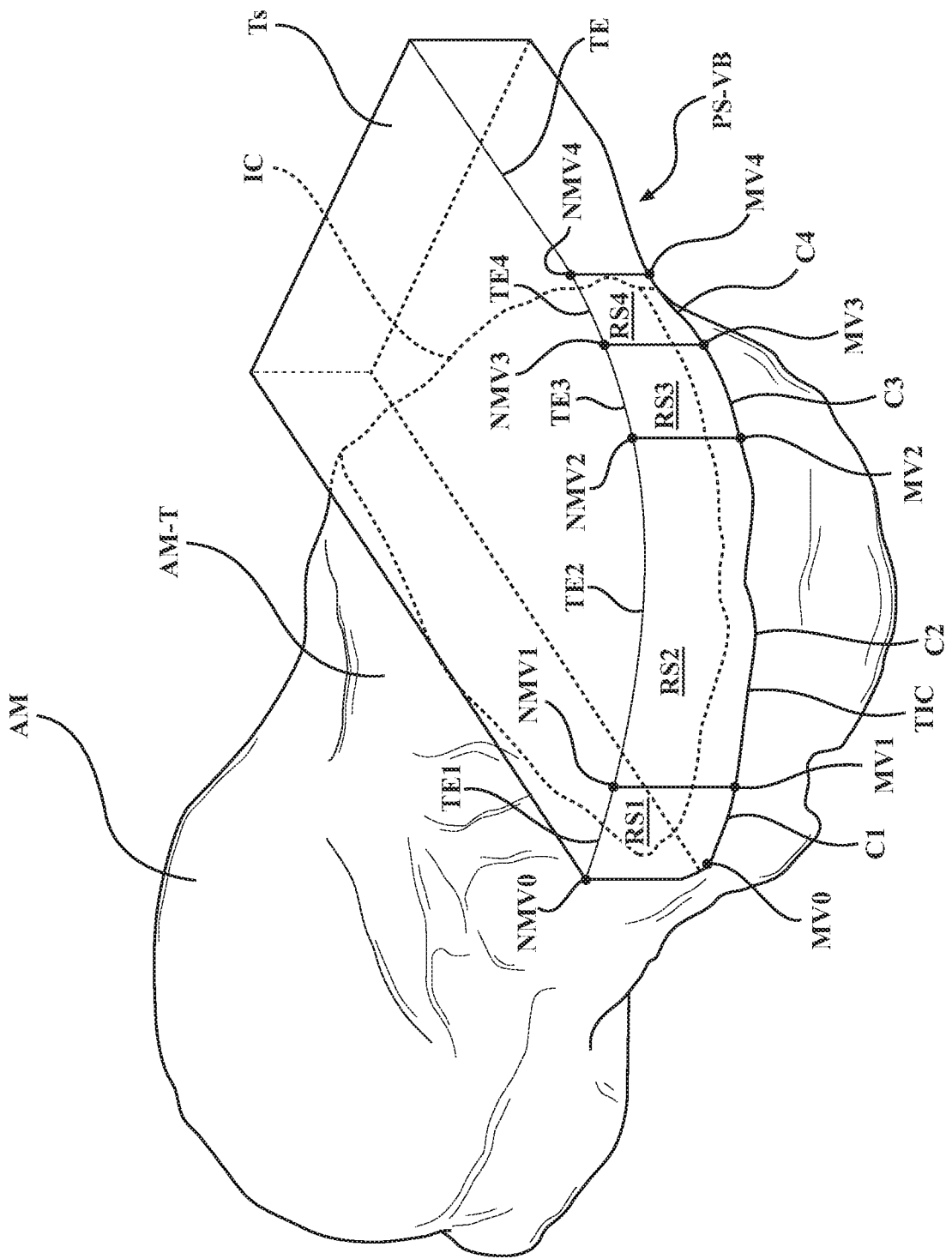
FIG. 9 illustrates the patient-specific virtual boundary derived from morphing the generic virtual boundary of FIG. 4, wherein portions of the patient-specific virtual boundary are designed to conform to the anatomical model.

Referring to FIG. 9, the patient-specific virtual boundary (PS-VB) is nearly formed. The morphable segments (C1)-(C4) are defined as the new bottom edges. The top edges (TE) remain in their original generic form. In other words, the new bottom edges are morphed while the top edges (TE) are fixed.

From this configuration, ruled surfaces (RS) are defined between the morphable segments (C) at the bottom and the top edges (TE) at the top. A ruled surface is a surface $S(t, u) = (1-u) p(t) + u q(t)$, where $0 \leq u \leq 1$ and $p(t)$ and $q(t)$ are two 3D curves with the same parameter domain. A ruled surface can be understood as a set of points swept by a moving line in parametric form. In this example, $p(t)$ is the bottom segment (C) and $q(t)$ is the top edge (TE) of the ruled surface.

The top edges (TE) of the ruled surfaces (RS) are generic because the ruled surfaces (RS) extend above the tallest portion (AM-T) of the anatomical model (AM), and hence, there is no need to morph these top edges (TE). The bottom segments (C) are morphed because the bottom edges of the ruled surfaces (RS) are dipped below the tallest portion (AM-T) of the anatomical model (AM). The ruling function creates a surface between these two edges.

In one example, the creation of the ruled surface takes into account the 3D shape of the anatomical model (AM) rather only than the intersection contour (IC) of the anatomical model (AM). For instance, the portion of the ruled surface (RS), in the region between the segment (C) and the tallest portion (AM-T) of the anatomical model (AM), is contoured to conform to the contoured side surface of the anatomical model (AM). In the region between the tallest portion (AM-T) of the anatomical model (AM) and the top edge (TE), the ruled surface (RS) can transition into the generic form, i.e., not contoured to match the contoured side surface of the anatomical model (AM).

In FIG. 9, the resulting ruled surfaces (RS1)-(RS4) are shown, where (RS4) is the last morphed ruled surface which transitions the morphed and non-morphed portions of, what is now, the patient-specific virtual boundary (PS-VB). In FIG. 9, the surface adjacent to (RS4) on the right is a transition surface to a non-morphed area. Such transition surfaces will be described below.

Each top edge (TE1-TE4) associated with ruled surfaces (RS1-RS4), respectively, can be defined between adjacent non-morphed vertices (NVM). Specifically, in FIG. 9, (TE1) is defined between (NMV0) and (NVM1), (TE2) is defined between (NMV1) and (NVM2), and so on. These vertices (NVM) are "non-morphed" because they are defined on the original top edge (TE), which in this example, is not morphed.

The ruled surfaces (RS) described above replace the original morphable side faces (F). Such replacement may be at the end of the operation described above, or may be done progressively. To execute this replacement, the geometric engines 72 can use any suitable function to replace faces, such as Parasolid LOPS function. The ruled surfaces (RS) can be converted into equivalent spline surfaces using the geometric engine 72.

The ruled surfaces (RS) can be merged together using the program 80. This can be done by the geometric engine 72 connecting all segments (C1)-(C4) together. The common underlying curve of these segments (C1)-(C4) is the intersection contour (IC), or portion thereof, and connection of these segments (C1)-(C4) is a smooth freeform curve. From this segment connection, a trimmed intersection contour (TIC) is determined. The trimmed intersection contour (TIC) is so named as it is a trimmed portion of the original intersection contour (IC). Such merging operations may also take into account any transition faces (T), which are described in detail below.

Notably, portions of the patient-specific virtual boundary (PS-VB) shown in FIG. 9 comprise the original (non-morphed) geometry from the generic virtual boundary (G-VB). Nevertheless, the virtual boundary (PS-VB) is still patient specific. The techniques described herein to do not require that all geometry of the generic virtual boundary (G-VB) be morphed. Instead, the morphed geometry may be that which has a tangible effect on the actual volume of bone resected by the surgical tool 20. Inconsequential portions of the generic virtual boundary (G-VB) may remain in original form. The ruled surfaces (RS) are also merged with these original portions from the generic virtual boundary (G-VB). The patient-specific virtual boundary (PS-VB) can be defined after all merging of surfaces is performed.

Clearly, as compared with the generic virtual boundary (G-VB) shown in FIG. 4, the patient-specific virtual boundary (PS-VB) shown in FIG. 9 has conformed to the outer edge/perimeter of the tibia. With the patient-specific virtual boundary (PS-VB), subsequent milling is appropriately constrained such that surrounding soft tissue can be preserved.

The example described above is focused primarily on morphing to account for the tibial case. Due to the practical realities of the tibial case wherein a constraint is often desired relative to exposed upper surface of the tibia, the generic virtual boundary (G-VB) is placed relative to the tallest portion (AM-T) of the anatomical model (AM) of the tibia. Hence, based on this relationship, the techniques described above primarily focus on morphing a bottom portion (e.g., bottom edge (BE) and base (B)) of the generic virtual boundary (G-VB).

However, the techniques described herein can be applied more broadly than this example, depending on the specific application. Hence, any portion(s) of the generic virtual boundary (G-VB) can be morphed. By the same note, the cross-sectional contour (IC) of the anatomical model (AM) can be computed based on intersecting the anatomical model (AM) with any portion of the generic virtual boundary (G-VB) besides the base (B).

For instance, if the generic virtual boundary (G-VB) is positioned beneath the lowest portion of the anatomical model (AM), i.e., from below), the cross-sectional contour (IC) of the anatomical model (AM) can be computed based on intersecting the anatomical model (AM) with a top surface (Ts) the generic virtual boundary (G-VB). Then, the top edge (TE) can be morphed and the bottom edge (BE) can remain generic. In another example, the generic virtual boundary (G-VB) is positioned relative to a feature protruding from the side of the anatomical model (AM) such that the protruding feature is located exclusively between (not extending past) the bottom edge (BE) and top edge (TE). In this example, the cross-sectional contour (IC) of the anatomical model (AM) can be computed based on intersecting the anatomical model (AM) with the side face (S) the generic virtual boundary (G-VB). Then, the bottom edge (BE) and top edge (TE) of the generic virtual boundary (G-VB) may remain generic, while a layer of the side face (S) is morphed. In yet another example, the generic virtual boundary (G-VB) may include a volume extending integrally below the base (B) to guide milling of an alignment post of the implant. This volume may be bottom-most part of the generic virtual boundary (G-VB) and remains generic or implant specific. However, the base (B), which in this case is not the bottom-most part of the generic virtual boundary (G-VB), is morphed to the cross-sectional contour (IC) of the anatomical model (AM). In other instances, the generic virtual boundary (G-VB) may be placed such both the base (B) and top surface (Ts) of generic virtual boundary (G-VB) intersect the anatomical model (AM). Here, there may be two intersection contours (IC), i.e., one based one intersection of the anatomical model (AM) with the top surface (Ts) and another based one intersection of the anatomical model (AM) with the base (B). Accordingly, both the bottom edge (BE) and top edge (TE) can be morphed.

Terms of relativity described herein, such as upper, lower, top, bottom, side, etc., are oriented with respect to the orientation of the elements drawn in the Figures. Such terms of relativity are provided for simplicity in description and are not intended to limit the capabilities, functions, or elements of the description. Indeed, the techniques described herein can be utilized on geometrical elements that are oriented in any manner.

2. Offset Version of Patient-Specific Virtual Boundary

In the example above, the patient-specific virtual boundary (PS-VB) was designed by morphing part of the generic virtual boundary (G-VB) to conform with the surface feature of the anatomical model (A) defined in part by the intersection contour (IC).

Figure 10:
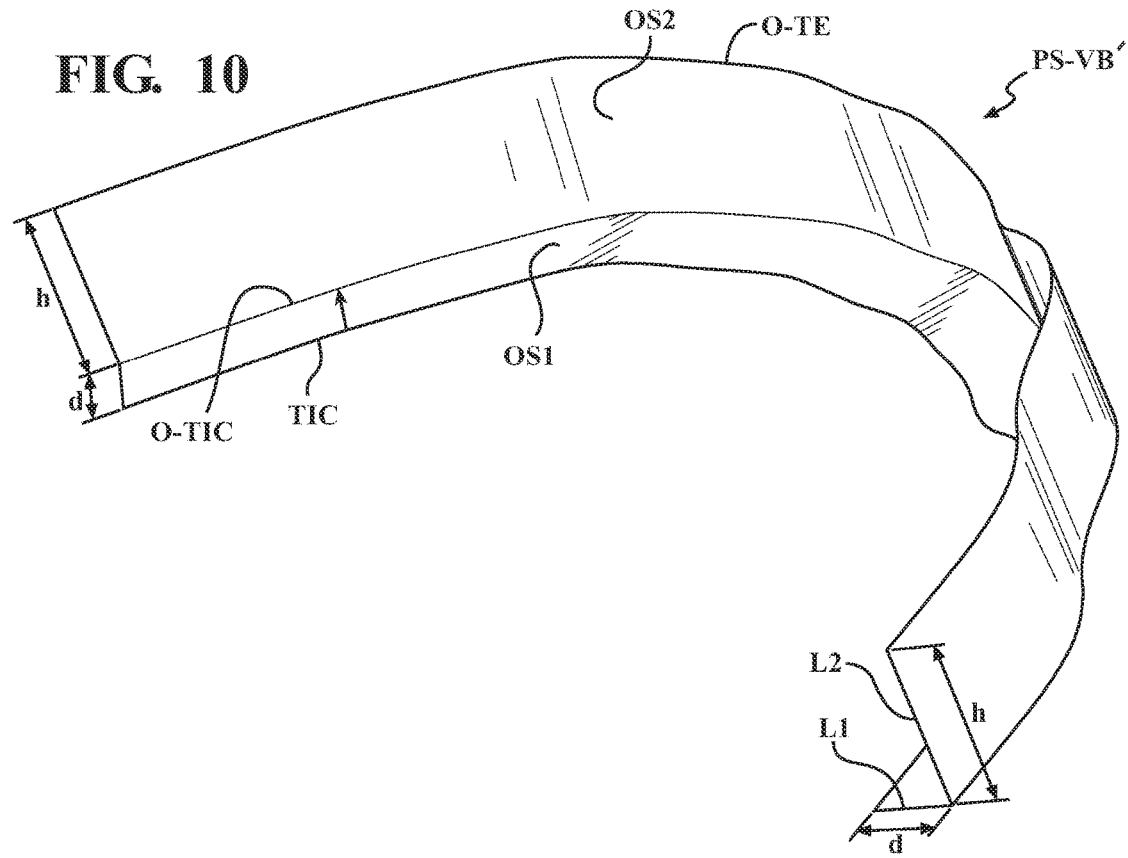
FIG. 10 is one example of offset surfaces that are morphed and are components of an offset version of the patient-specific virtual boundary.
Figure 11:
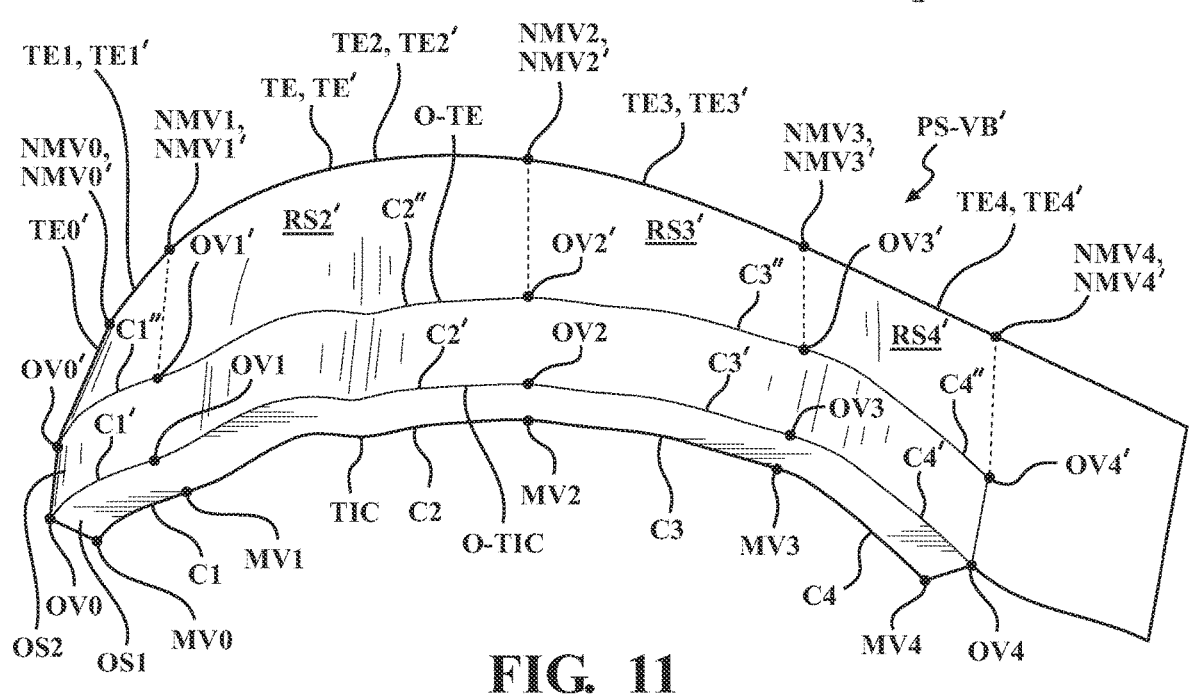
FIG. 11 illustrates the offset surfaces of FIG. 10 combined with additional (ruled) surfaces to further define the offset version of the patient-specific virtual boundary, according to one example.
Figure 12:
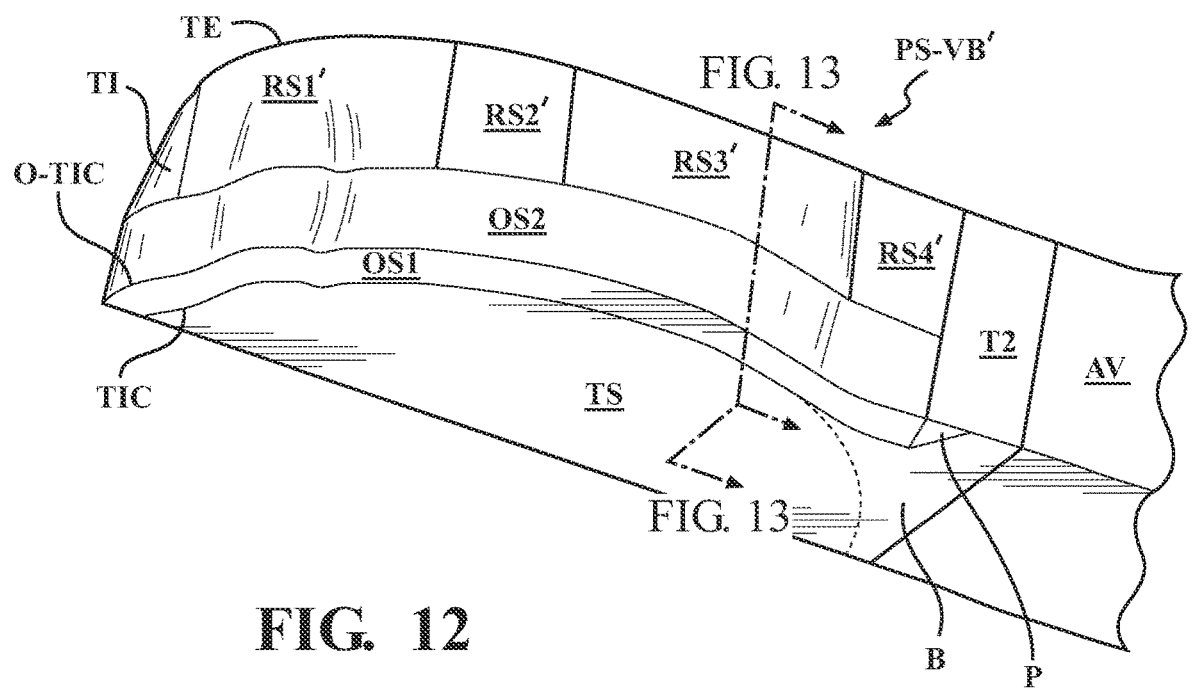
FIG. 12 illustrates the surfaces of FIG. 11 combined with other virtual constraint objects, such as non-morphed portions from the generic virtual boundary, transition surfaces, patch surfaces, and a portion of the greater allowed volume to define the offset patient-specific virtual boundary, according to one example.

With reference to FIGS. 10-12, the patient-specific virtual boundary (PS-VB) can further be designed with one or more surfaces that are spaced apart from the surface feature of the anatomical model (AM) by an offset distance, thereby producing an offset patient-specific virtual boundary (PS-VB').

Some of the geometrical objects from the non-offset version of the patient-specific virtual boundary (PS-VB) are utilized to produce the offset patient-specific virtual boundary (PS-VB'). Hence, any description above with respect to any aspect of the patient-specific virtual boundary (PS-VB) can be applied fully and equally to the offset patient-specific virtual boundary (PS-VB'), as described in this section.

In one example, the offset distance accounts for, or is specifically designed to accommodate, a geometric feature of a surgical tool 20. The geometric feature of the surgical tool 20 may comprise the shape of the cutting part of the tool 20, a range of motion of the tool 20, or other parts of the tool 20 that do perform cutting, e.g., the shaft or handle. For example, when the tool 20 comprises a spherical burr 25, the offset distance may be a radius of the spherical burr 25. Such offsets can assist with ensuring that milling of the anatomical volume (A) in accordance with the offset patient-specific virtual boundary (PS-VB') produces a result that takes into account the actual milling properties of the tool 20 such that precisely the right amount of volume is resected. In other examples, the offset distance can be based on a configurable default value, e.g., 1 mm from bone edge, or the like.

To generate the offset patient-specific virtual boundary (PS-VB'), the system 10, software program 80, and geometric engine 72 can execute the following steps, according to one example.

In FIG. 9, segments (C1)-(C4), which are a portion of the intersection contour (IC), are connected to define the trimmed intersection contour (TIC), which is a partial outline of the trimmed surface/face (TS). The patient-specific virtual boundary (PS-VB) is not yet offset.

In FIG. 10, the trimmed intersection contour (TIC) (from FIG. 9) is offset to produce an offset trimmed intersection contour (O-TIC). This offset can be a planar offset within the corresponding plane of the intersection contour (IC). The trimmed intersection contour (TIC) can be offset by either expanding the trimmed intersection contour (TIC) or retracting the trimmed intersection contour (TIC). Moreover, the trimmed intersection contour (TIC) can be offset in any suitable direction and according to any suitable technique, such as planar offsetting, or the like.

As described above, the trimmed surface/face (TS) may be defined from the reference surface (E). Moreover, the intersection contour (IC) and trimmed intersection contour (TIC) can be components of the trimmed surface/face (TS). Accordingly, the system 10 may utilize the trimmed off regions of the reference surface (E) to provide a geometric foundation to virtually extend the trimmed intersection contour (TIC) to define the offset trimmed intersection contour (O-TIC). In other words, the intersection contour (IC) can be extended within the plane of the reference surface (E). Alternatively, the intersection contour (IC) can be defined using other techniques.

For tibial applications, the trimmed intersection contour (TIC) and the offset trimmed intersection contour (O-TIC) are planar and coincident to the footprint (FP) plane. Mainly, in this example, the trimmed intersection contour (TIC) and the offset trimmed intersection contour (O-TIC) are derived commonly from the same extendable planar surface (E). However, these contours may be non-coplanar depending on many factors, such as the contour of the anatomical volume (AV), the shape of the reference surface (E), the nature of the offset, and the like. Furthermore, offsetting need not require the reference surface (E), but can be performed by other geometric operations.

To produce the geometry of the offset patient-specific virtual boundary (PS-VB'), two line segments (L1), (L2) are defined in this example. Line segment (L1) is defined between the trimmed intersection contour (TIC) and the offset trimmed intersection contour (O-TIC). Line segment (L1) is coincident to the footprint (FP) plane and the length of line segment (L1) is equal to the offset distance (d). In this example, the offset distance (d) is set to the radius of the burr 25. Thus, the offset trimmed intersection contour (O-TIC) is offset from the trimmed intersection contour (TIC) by radius of the burr 25. The offset distance (d) can be set at other values relating to the tool 20, or otherwise.

Line segment (L2) defines the height of a surface aligned with the offset trimmed intersection contour (O-TIC). Line segment (L2) is orthogonal to footprint (FP) plane and starts at the end point of (L1) thereby forming an L-shape between (L1) and (L2). Line segment (L2) defines a height (h). In this example, the height (h) is twice the radius of the burr 25. The height (h) can be set at other values relating to or not relating to the radius.

The example above describes using orthogonal line segments for generating the offset patient-specific virtual boundary (PS-VB'). However, depending on the nature of the offset, among other things, geometry other than orthogonal line segments may be utilized to generate the offset patient-specific virtual boundary (PS-VB'). For example, offsetting may be done with non-orthogonal line segments, parallel segments, curved segments, etc. Moreover, offsetting need not be limited to the directions of (d) and (h) described above and can be in any suitable direction.

From line segments (L1) and (L2), corresponding surfaces are generated to form the offset patient-specific virtual boundary (PS-VB'). Specifically, offset surfaces (OS1) and (OS2) are generated from line segments (L1) and (L2), respectively. In this example, surfaces (OS1) and (OS2) are orthogonal to one another because line segments (L1) and (L2) are orthogonal. Line segment (L1) is coincident with offset surface (OS1) and line segment (L2) is coincident with offset surface (OS2). Both of these offset surfaces (OS) are patient-specific and morphed because they are derived from the underlying intersection contour (IC) derived directly from the anatomical model (AM) geometry. The offset surfaces (OS) may alternatively be defined as offset faces. Furthermore, the term "offset surface" does not require offsetting a surface. Instead, a curve can be offset and the offset surfaces (OS) can be generated based on the offset curve, as will be described below.

Here, the offset surface (OS1) forms part of the bottom surface of the offset patient-specific virtual boundary (PS-VB'). Offset surface (OS1) is defined between the trimmed intersection contour (TIC) and the offset trimmed intersection contour (O-TIC) and has a width of the offset distance (d). Offset surface (OS1) will replace or extend the trimmed surface/face (TS) from FIG. 9.

Offset surface (OS2) forms part of the side surface of the offset patient-specific virtual boundary (PS-VB'). Offset surface (OS2) is defined between the offset trimmed intersection contour (O-TIC) and a top edge (O-TE), and has height (h). Offset surface (OS2) will replace the ruled surfaces (RS1)-(RS4) that were merged together in FIG. 9.

To create these offset surfaces (OS), the geometric engine 72 is configured to sweep a planar profile along a curve. More specifically, in this example, the planar profile L-shape shown in FIG. 10 that is formed by segments (L1) and (L2) is swept along the trimmed intersection contour (TIC). The planar profile L-shape and orientation with respect to the intersection contour (TIC) does not change during the sweep.

The geometric engine 72 can sweep any shaped profile along any path to form the offset surfaces (OS). Sweeping can be translational or rotational and may include one or more sweep surfaces. The profile can change shape during the sweep. Moreover, sweeping may be along curves other than the trimmed intersection contour (TIC), such as long the offset trimmed intersection contour (O-TIC), or the like.

As an alternative to sweeping, the geometric engine 72 may generate the offset surfaces (OS) by extruding geometry, such as extruding the offset trimmed intersection contour (O-TIC) by any appropriate length, such as twice the radius.

The outcome of the above-described process is a portion of the offset patient-specific virtual boundary (PS-VB'), comprising patient-specific and offset surfaces (OS1) and (OS2).

At this stage, the offset surfaces (OS) can be integrated with geometrical objects from the non-offset version of the patient-specific virtual boundary (PS-VB) of FIG. 9. In this example, the top edge (O-TE) of the offset surface (OS2) falls short of the top edge(s) (TE) of the side surface of the patient-specific virtual boundary (PS-VB) in FIG. 9. Moreover, the offset trimmed intersection contour (O-TIC) is morphed while the top edges (TE) are fixed and remaining in their generic form.

Referring now to FIG. 11, the system 10 with the aide of the geometric engine 72 is configured to generate additional surfaces to connect the offset surface (OS2) to the original top edge (TE) (from FIG. 9), thereby further defining the offset patient-specific virtual boundary (PS-VB').

In one example, the non-morphed vertices (NMV) on the original top edge (TE) of FIG. 9 are mapped to the top edge (O-TE) of the second offset surface (OS2). Such mapping can be performed, for example, by the orthogonal projection of each non-morphed vertex (NMV) onto the top edge (O-TE) of the second surface (OS2). The result of this mapping can define offset vertices (OV') on the top edge (O-TE) of the offset surface (OS2). Between adjacent offset vertices (OV'), a set of offset segments (C") can be defined on the top edge (O-TE) of the offset surface (OS2). From here, ruled surfaces (RS') are built by the geometric engine 72 to transition between the original top edge (TE) and the top edge (O-TE) of the offset surface (OS2). More specifically, in this example, (RS1') is defined between (TE1) and (C1"), (RS2') is defined between (TE2) and (C2"), and so on.

In another example, the segments (C) from the trimmed intersection contour (TIC) of FIG. 9 can be utilized. For each curved segment (C1)-(C4), the geometric engine 72 determines corresponding offset segments (C') on the offset surface (OS2). As shown, a first set of offset segments (C') are defined on the offset trimmed intersection contour (O-TIC) and a second set of offset segments (C") are defined on the top edge (O-TE) of the offset surface (OS2). Offset segments (C') are planar with curved segment (C) and offset segments (C") are orthogonal or more specifically, parallel, to both (C) and (C'). Segments (C), (C') and (C") are all patient-specific because they have been morphed based on the geometry of the trimmed intersection contour (TIC).

Notably, it may not be necessary for the geometric engine 72 to determine both of the offset segments (C') and (C") since these segments all reside on the offset surface (OS2), and hence there is some redundancy. Nevertheless, for illustrative purposes, both offset segments (C') and (C") are described below.

The offset segments (C') and (C") can be determined using any suitable technique employed by the geometric engine 72, such as the mapping function described with reference to FIG. 8. For example, a set of offset vertices (OV) on the offset trimmed intersection contour (O-TIC) can be mapped to morphed vertices (MV) on the trimmed intersection contour (TIC). Similarly, offset vertices (OV') on the top edge (O-TE) of the offset surface (OS2) can be mapped to offset vertices (OV) on the offset trimmed intersection contour (O-TIC). In this example, offset vertices (OV0-OV4) and (OV0'-OV4') are mapped from morphed vertices (MV0-MV4). One example of performing this mapping can include assigning (or mapping) each point (MV) to a corresponding point/vertex (OV) on the offset trimmed intersection contour (O-TIC) by defining a plane orthogonal to the trimmed intersection contour and coincident with the vertex (MV) and determining the offset vertex (OV) as intersection point of that plane and the offset curve (O-TIC). Similarly, offset vertices (OV') on the top edge (O-TE) can be produced by mapping from (OV) to (OV').

Between adjacent offset vertices (OV0-OV4), the geometric engine 72 generates offset segments (C1'-C4') along the offset trimmed intersection contour (O-TIC). Between adjacent offset vertices (OV0'-OV4'), the geometric engine 72 generates offset segments (C1"-C4") along the top edge (O-TE) of the offset surface (OS2).

From the offset segments (C1"-C4"), another mapping can be performed to obtain corresponding segments at the original top edge (TE). Here, non-morphed vertices (NMV) on the original top edge (TE) can be mapped from the offset vertices (OV') to the closest point on the original top edge (TE), e.g., by using any of the mapping techniques described herein. The result of this mapping is corresponding non-morphed vertices (NMV0'-NVM4') having top edge segments (TE1'-TE4') defined therebetween. Although top edge segments (TE1'-TE4') are on the original top edge (TE), they need not necessarily correspond to top edge segments (TE1-TE4) from FIG. 9. Similarly, non-morphed vertices (NMV0'-NVM4') may or may not correspond to non-morphed vertices (NMV0-NMV4) from FIG. 9. In this example, all original top edge segments (TE1-TE4) or (TE1'-TE4') can be morphed into one smooth curve, i.e. top edge (TE) or top edge (TE').

The geometric engine 72 can define the top edge segments (TE1'-TE4') using other suitable geometric technique. For example, the geometric engine 72 may alternatively map from the curved segments (C) directly to the original top edge (TE) without intermediary steps of mapping from the curved segments (C) to offset segments (C') to offset segments (C"). In addition, the geometric engine 72 may map from the offset segments (C') or offset segments (C") directly to the original top edge (TE). Moreover, the top edge segments (TE') may be defined according to geometric functions other than mapping, such as approximation methods.

From here, ruled surfaces (RS') are built by the geometric engine 72 to transition between the top edge (O-TE) of the offset surface (OS2) and the original top edge (TE). The ruled surfaces (RS') can be defined between any of the "patient-specific" segments described above, (C), (C') or (C") and the top edge segments (TE or TE'). In FIG. 11, ruled surfaces (RS') are formed between offset segments (C") and top edge segments (TE or TE'), resulting in ruled surfaces (RS1'-RS4') (RS1' not labeled in FIG. 11 for simplicity in illustration). In one example, the ruled surface (RS') is formed using the shortest possible path between top edge (O-TE) of the offset surface (OS2) and the original top edge (TE). Alternatively, or additionally, any of these ruled surfaces (RS') can be contoured to match the contoured side surface of the anatomical model (AM).

Figure 13:
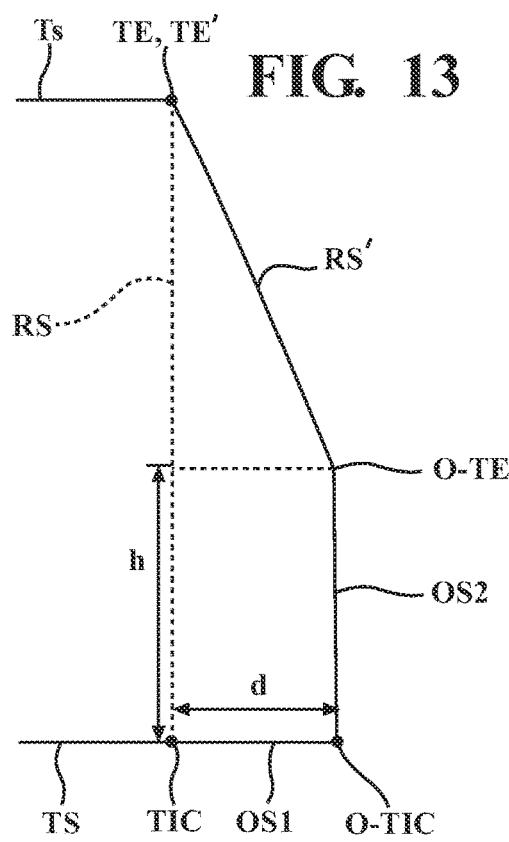
FIGS. 13-16 illustrate cross-sectional views of different examples of the offset patient-specific virtual boundaries.

FIG. 13 is a cross-sectional view of the offset patient-specific virtual boundary (PS-VB') taken from the perspective identified in FIG. 12. Although the prior ruled surface (RS) from FIG. 9 is replaced by (RS') and (OS2) in this example, the offset cross-sectional area is visualized with reference to the prior ruled surface (RS) for comparative purposes. Here, the offset cross-sectional area is the area bounded by (RS), (RS'), (OS1) and (OS2).

Although segments (C), (C') or (C") are referenced herein to explain examples related to generation of the ruled surfaces (RS'), it is not required to segment the trimmed intersection contour (IC), offset trimmed intersection contour (O-TIC) or the top edge (O-TE) of the offset surface (OS2) to generate the ruled surfaces (RS'). Instead, ruling can be defined between (unsegmented) original top edge (OE) and unsegmented versions of the trimmed intersection contour (IC), offset trimmed intersection contour (O-TIC) or the top edge (O-TE) such that there is contiguous ruled surface (RS').

Referring to FIG. 12, the geometric engine 72 can produce one or more transition surfaces (T) between the offset patient-specific virtual boundary (PS-VB') and other constraints, such as portions of the allowed volume (AV) or any corresponding original generic geometry for which morphing is not necessary (e.g., the base (B) or side surface (S) of the generic virtual boundary (G-VB)). In FIG. 12, these transition surfaces (T) are defined adjacent the ruled surfaces (RS') or the offset surfaces (OS2). Specifically, in FIG. 12, transition surface (T1) transitions the offset patient-specific virtual boundary (PS-VB') to a backside surface of the virtual boundary (opposite OS2 and ruled surfaces RS'). Transition surface (T2) transitions the offset patient-specific virtual boundary (PS-VB') to the greater allowed volume (AV). Transition surfaces (T) can be patient-specific or generic.

Depending on the interplay of the various geometries described herein, any shape and number of transition surfaces (T) may be utilized. The transition surfaces (T) may also provide transitions between surfaces other than those described herein. Moreover, transition surfaces (T) may be utilized for the non-offset version of the patient-specific virtual boundary (PS-VB).

Furthermore, there may be residual openings in the surface of the offset patient-specific virtual boundary (PS-VB') that should be closed to ensure the boundary is complete and "sealed". In this case, one opening is illustrated adjacent the base (B) surface in the transition (T2) region. The geometric engine 72 closes the opening by merging a patch surface (P) with the adjoining surfaces. Patch surfaces (P) can be patient-specific or generic and may be utilized for the non-offset version of the patient-specific virtual boundary (PS-VB).

In FIG. 12, the geometric engine 72 merges the ruled surfaces (RS'), the offset surfaces (OS1) and (OS2), the original top edge (TE), the trimmed surface/face (TS), the transition surfaces (T), the patch surfaces (P), and any corresponding original generic geometry for which morphing is not necessary (e.g., portions of the base (B) or side surface (S) of the generic virtual boundary (G-VB)). A final version of one example of the offset patient-specific virtual boundary (PS-VB') is produced.

As compared with the (non-offset) patient-specific virtual boundary (PS-VB) shown in FIG. 9, the offset patient-specific virtual boundary (PS-VB') shown in FIG. 12 has been offset from the outer edge perimeter of the tibia using the offset surfaces (OS). By accounting for the burr 25 radius, the offset patient-specific virtual boundary (PS-VB') ensures that enough bone can be removed while preserving adjacent soft tissue.

Figure 14:
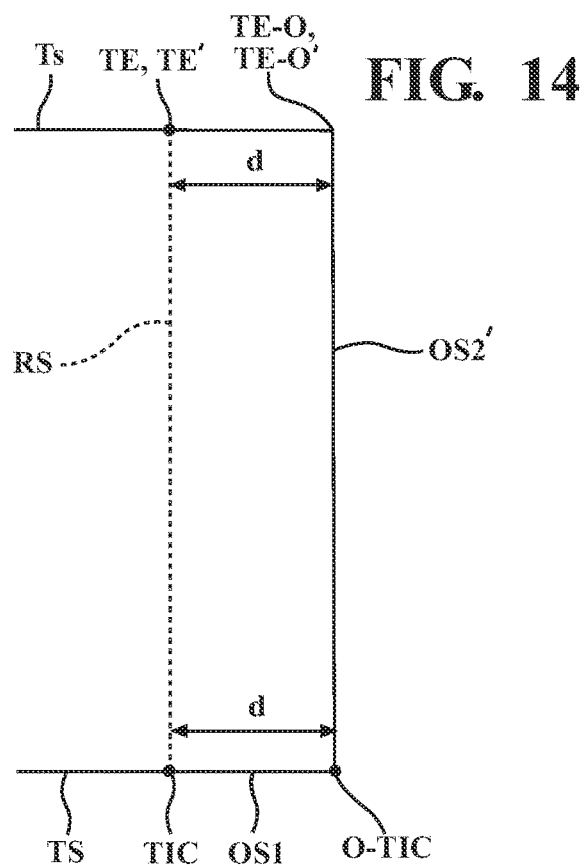
Figure 15:
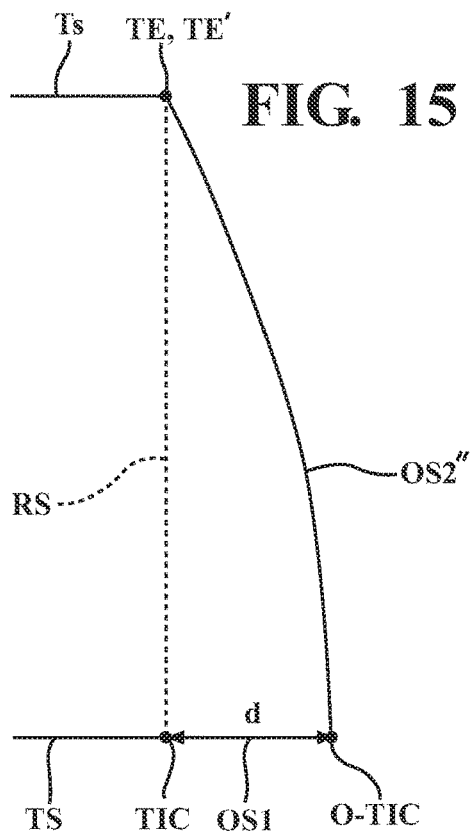
Figure 16:
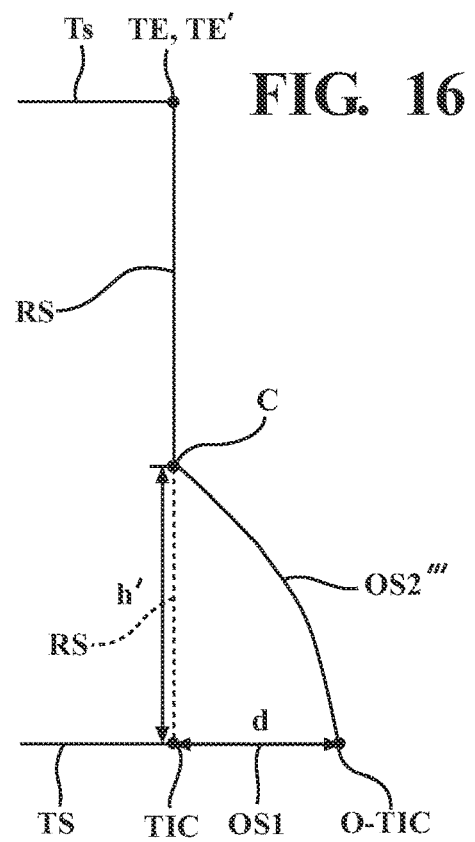

There are methods of generating the offset patient-specific virtual boundary (PS-VB') in addition or alternative to those described above. For example, FIGS. 14-16 illustrate cross-sectional views of different examples of the offset patient-specific virtual boundary (PS-VB') taken from the perspective identified in FIG. 12. Again, the offset cross-sectional area is visualized with reference to the prior ruled surface (RS) for comparative purposes.

In the example of FIG. 14, the offset patient-specific virtual boundary (PS-VB') can be formed by offsetting both the trimmed intersection contour (TIC) and the top edge (TE), e.g., as shown in FIG. 9. The trimmed intersection contour (TIC) is offset to the offset trimmed intersection contour (O-TIC) and the top edge (TE) is offset to an offset top edge (TE-O). Alternatively, for any of the example of FIGS. 13-16, top edge (TE') from FIG. 11 and offset top edge (TE-O') can be utilized. Both of these offsets are performed by the same offset distance (d). An alternative version of the second offset surface (OS2') can be defined directly between the offset trimmed intersection contour (O-TIC) and the offset top edge (TE-O, TE-O'). Accordingly, the second offset surface (OS2') forms the entire (exterior) side surface of the offset patient-specific virtual boundary (PS-VB') in this cross-section. The second offset surface (OS2') can be formed using any suitable technique, such as extrusion, sweeping, ruled surface operations, or by shortest possible path. The height (h) of the second offset surface (OS2') in this example is the shortest distance between the offset-trimmed intersection contour (O-TIC) and the correspondingly offset top edge (TE-O, TE-O') or the shortest distance between the trimmed intersection contour (TIC) and the top edge (TE, TE'). Here, the second offset surface (OS2') will be perpendicular to (OS1) because both (O-TIC) and the offset top edge (TE-O, TE-O') are offset by the same distance (d). However, the offset distances can be different for (O-TIC) and the offset top edge (TE-O, TE-O') resulting in the angle between the second offset surface (OS2') and (OS1) being less than or greater than 90 degrees.

In the example of FIG. 15, the offset patient-specific virtual boundary (PS-VB') can be formed by offsetting the trimmed intersection contour (TIC) by distance (d), while maintaining top edge (TE, TE') in original, non-offset, form. Yet another version of the second offset surface (OS2") is defined directly between (non-offset) top edge (TE, TE') and the offset-trimmed intersection contour (O-TIC). Accordingly, the second offset surface (OS2") forms the entire (exterior) side surface of the offset patient-specific virtual boundary (PS-VB') in this cross-section. Again, (OS2") can be formed by any suitable operation. Here, the angle between the first offset surface (OS1) and the second offset surface (OS2") will be less than 90 degrees because the (O-TIC) is offset by (d), whereas the top edge (TE, TE') is not offset.

In yet another example, as shown in FIG. 16, the offset patient-specific virtual boundary (PS-VB') can be formed by specifying a portion of the original ruled surface(s) (RS) of FIG. 9 from which the offset will be based. This portion can be delineated using a curve (C) that extends along the ruled surfaces (RS) at a specified height (h'). Height (h') can be defined between the trimmed intersection contour (TIC) and the original top edge (TE, TE'). Here, height (h') is less than the distance between (TIC) and (TE, TE'). Height (h') can be specified based on factors described herein for offset height (h), e.g., see FIG. 10, and/or based on other factors, such as the height of the upper surface (AM-T) of the anatomical model (AM) adjacent to or intersecting the ruled surface (RS) region. As with the other examples, the trimmed intersection contour (TIC) is offset to the offset trimmed intersection contour (O-TIC). Another version of the second offset surface (OS2''') is defined directly between the offset-trimmed intersection contour (O-TIC) and the curve (C), using any suitable method. Since height (h') is less than the distance between (TIC) and (TE, TE'), the original ruled surface (RS) remains in tact. The second offset surface (OS2''') can be combined with the original ruled surface (RS) to define the (exterior) side surface of the offset patient-specific virtual boundary (PS-VB') in this cross-section. Again, the angle between the first offset surface (OS1) and the second offset surface (OS2''') will be less than 90 degrees because the (O-TIC) is offset by (d), whereas curve (C) is defined on the original (non-offset) ruled surface (RS).

While the specification has been drafted to distinguish the (non-offset) patient-specific virtual boundary (PS-VB) shown in FIG. 9 from the offset patient-specific virtual boundary (PS-VB') shown in FIG. 12, any features, characteristics or results described in relation to the (non-offset) patient-specific virtual boundary (PS-VB) can be applied fully to the offset patient-specific virtual boundary (PS-VB'), and vice-versa. Indeed, both virtual boundaries are patient-specific and provide technical solutions over the prior art configurations. However, the offset patient-specific virtual boundary (PS-VB') comprises the additional features relating to offsetting, as described above.

Figure 17:
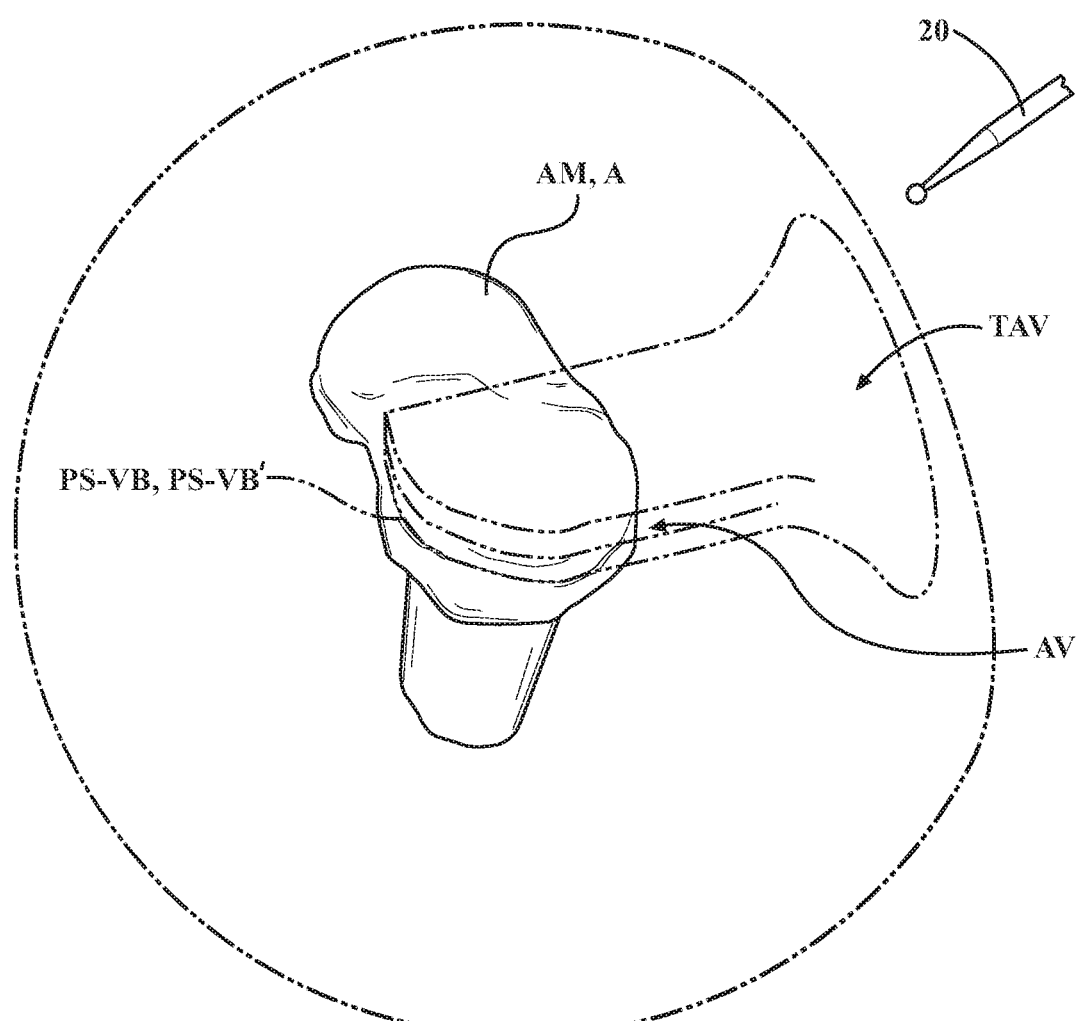
FIG. 17 illustrates the patient-specific virtual boundary or offset patient-specific boundary as a component of a greater allowed volume for constraining the surgical tool.

FIG. 17 illustrates how the generic virtual boundary (G-VB) of FIG. 5 is replaced by either the patient-specific virtual boundary (PS-VB) or offset patient-specific virtual boundary (PS-VB') according to the techniques described herein. The patient-specific virtual boundary (PS-VB, PS-VB') is integrated with the allowed volume (AV) and tool access volume (TAV) for defining one example of a virtual constraint on motion of the tool 20 relative to the anatomical model (AM), and consequently, relative to the anatomy (A) when the anatomical model (AM) is registered to the anatomy (A).

Figure 18:
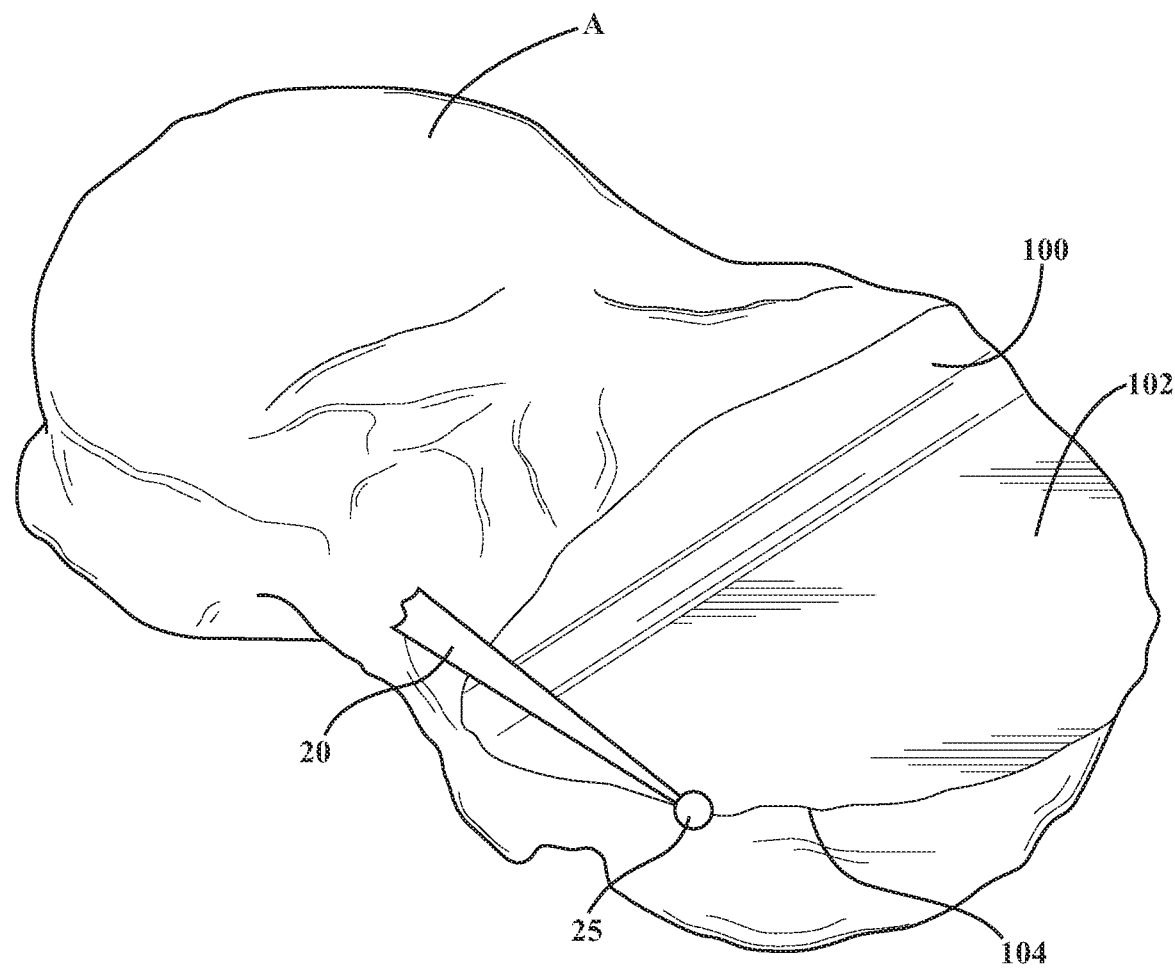
FIG. 18 illustrates an example outcome of milling a portion of the physical anatomy (tibia) according to a surgical plan utilizing the offset patient-specific virtual boundary of FIG. 12 or 17.

FIG. 18 illustrates one example of the physical anatomy (A) that is resected with the tool 20 according to a surgical plan wherein the offset patient-specific virtual boundary (PS-VB') of FIG. 12 or FIG. 17 is defined relative to the anatomical model (AM). The resected volume is removed to accommodate an onlay implant for a tibial distal case. As shown, milling according to the offset patient-specific virtual boundary (PS-VB') results in resected surfaces 100 and 102. Resected surface 100 is the vertical wall portion that is defined as the result of milling along the rear wall (not shown) of the offset patient-specific virtual boundary (PS-VB'). More significantly, resected surface 102 is the horizontal portion that is defined as the result of milling with the burr 25 along the trimmed surface/face (TS), bound by offset surfaces (OS1), (OS2). The horizontal resected surface 102 is milled flat to the outer edge 104. The requisite volume has been completely and accurately milled to accommodate the tibial implant. At the same time, because offset surfaces (OS1), (OS) accommodate the burr 25 radius, milling remains patient-specific while preserving soft tissue in sensitive overhang region adjacent to the outer edge 104.

D. Graphical User Interface

The software program 80 is optionally configured with instructions, which when executed by one or more of the processors 70, optionally implements a graphical user interface (GUI) 96. In one example, the GUI 96 is implemented by the clinical application 74. The GUI 96 can be displayed on any of the displays 38 of the system 10 and can receive input from any of the input devices 40, 42.

The GUI 96 may provide visualization for viewing or design of any of the aforementioned features of the morphing techniques. Any version of the Figures illustrated herein showing various virtual boundaries and geometries may be displayed using the GUI 96. However, many of the Figures are provided merely for enabling understanding of the constraint morphing technique and can be performed by the software program 80 without visualization.

The GUI 96 may take clinical or high-level input from the surgeon, and use this information to compute the lower-level settings used for generating the patient-specific virtual boundary (PS-VB). In other words, the settings may be specified indirectly based on the user input.

The GUI 96 may provide an interface to enable the user to selectively design and/or input control parameters relating to any of the boundaries or morphing processes described herein. In other examples, however, the surgeon would not directly design or specify such parameters. Rather, the surgeon would use the GUI 96 primarily to position the implant model (IM) relative to the anatomical model (AM).

Various control parameters can be adjusted using the GUI 96. The control parameters can be designed offline and included as part of the implant plan, and the user (surgeon) views/approves the plan prior to execution.

One example control parameter is a tolerance parameter. One tolerance parameter is fitting tolerance, which enables the user to define the tolerance used to approximate a polygon by a spline curve. The fitting tolerance parameter can manipulate spline curve approximation of the intersection contour (IC) or any morphed faces or surfaces derived therefrom. Another tolerance parameter is modeling tolerance, which enables the user to select a tolerance used for 3D modeling operations. Such modeling operations can include intersection operations, surface creation, and the like. Another tolerance parameter is milling tolerance. This parameter is used to define tolerance for sweep operations to create the offset surfaces (OS), as described above, which are provided to enable patient-specific milling that accounts for the geometric feature of the tool 20. These tolerance parameters can be adjusted using any unit of measurement, such as millimeters.

The GUI 96 can also provide settings that relate to planning or generation of the patient-specific virtual boundary (PS-VB), such as defining generation parameters for any of the surfaces, edges, transitions, patches, etc.

Other parameters may include tool parameters. Tool parameters include any settings relating to the tool 20, such as setting a geometric feature of the tool 20. The geometric feature can be the type of energy applicator 24, etc. For example, where the energy applicator 24 is the burr 25, the GUI 96 enables inputting of the radius (r) of the burr 25. Using this parameter, the software program 80 can autogenerate various features described above, such as the offset distance (d), height (h), or the like. Alternatively, the user may not enter these parameters directly into the GUI 96, but rather the system would allow the parameters to be configured in the software via configuration file, automatically read from built-in memory in the energy applicator, tool, or burr, etc.

Other parameters that can be set by the GUI 96 can relate to the milling path defined in accordance with the virtual boundary, such as those parameters described in U.S. Provisional Patent Application No. 62/685,476, filed on Jun. 15, 2018, the contents of which is incorporated by reference herein in its entirety The GUI 96 is optional, and the path generation techniques described herein can take place without user interaction. In such instances, tool or implant parameters may be stored in memory and retrieved from memory. The GUI 96 may have features other than those described herein.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A computer-implemented surgical planning method, comprising:

obtaining a generic virtual boundary comprising a generic surface with a generic edge;

positioning the generic virtual boundary relative to a virtual anatomical model such that the generic surface intersects the virtual anatomical model;

computing an intersection of the generic surface and the virtual anatomical model to define a cross-sectional contour of the virtual anatomical model;

morphing the generic edge to the cross-sectional contour to produce a customized surface with a patient-specific edge;

generating a customized face extending from, and along, the patient-specific edge;
producing a patient-specific virtual boundary by merging the customized surface and the customized face; and
configuring the patient-specific virtual boundary for providing a constraint on movement and/or operation of a surgical tool in response to the surgical tool interacting with the patient-specific virtual boundary.

2. The computer-implemented surgical planning method of claim 1, wherein the generic surface is further defined as a first generic surface and the generic edge is further defined as a first generic edge, the method comprising:
obtaining the generic virtual boundary comprising the first generic surface with the first generic edge, and a second generic surface with a second generic edge.

3. The computer-implemented surgical planning method of claim 2, comprising:
positioning the generic virtual boundary relative to the virtual anatomical model such that the first generic surface intersects the virtual anatomical model;
computing the intersection of the first generic surface and the virtual anatomical model to define the cross-sectional contour of the virtual anatomical model;
morphing the first generic edge to the cross-sectional contour to produce the customized surface with the patient-specific edge;
maintaining a geometry of the second generic surface and the second generic edge;
generating the customized face extending along the patient-specific edge and extending between the patient-specific edge and the second generic edge; and
producing the patient-specific virtual boundary by merging the customized surface, the second generic surface, and the customized face.

4. The computer-implemented surgical planning method of claim 2, comprising:
positioning the generic virtual boundary relative to the virtual anatomical model such that both the first generic surface and the second generic surface intersect the virtual anatomical model;
computing the intersection of the first generic surface and the virtual anatomical model to define a first cross-sectional contour of the virtual anatomical model;
morphing the first generic edge to the first cross-sectional contour to produce a first customized surface with a first patient-specific edge;
computing the intersection of the second generic surface and the virtual anatomical model to define a second cross-sectional contour of the virtual anatomical model;
morphing the second generic edge to the second cross-sectional contour to produce a second customized surface with a second patient-specific edge;
generating the customized face extending between, and along, the first patient-specific edge and the second patient-specific edge; and
producing the patient-specific virtual boundary by merging the first customized surface, the second customized surface, and the customized face.

5. The computer-implemented surgical planning method of claim 2, comprising:
obtaining the generic virtual boundary with both the first generic surface and the second generic surface being planar and having the first generic surface being spaced apart from, and being parallel to, the second generic surface.

6. The computer-implemented surgical planning method of claim 1, comprising:
obtaining the generic virtual boundary having a geometry derived from a virtual implant model.

7. The computer-implemented surgical planning method of claim 1, wherein morphing the generic edge to the cross-sectional contour comprises:
morphing the generic edge to be coincident to the cross-sectional contour to produce the patient-specific edge.

8. The computer-implemented surgical planning method of claim 1, wherein morphing the generic edge to the cross-sectional contour comprises:
morphing the generic edge to a contour being similar to the cross-sectional contour and the contour being spaced apart from the cross-sectional contour by an offset distance, and wherein the contour corresponds to the patient-specific edge.

9. The computer-implemented surgical planning method of claim 8, wherein the offset distance is derived from a geometric feature of the surgical tool.

10. The computer-implemented surgical planning method of claim 1, comprising:
generating the customized face to extend perpendicularly relative to the customized surface.

11. The computer-implemented surgical planning method of claim 1, comprising generating the customized face by:
producing ruled surfaces along the patient-specific edge; and
merging the ruled surfaces.

12. The computer-implemented surgical planning method of claim 1, wherein producing the patient-specific virtual boundary occurs automatically and intra-operatively.

13. The computer-implemented surgical planning method of claim 1, comprising:
obtaining a pre-operative plan including the generic virtual boundary having a geometry derived from a virtual implant model, and having the generic virtual boundary positioned at a first location relative to the virtual anatomical model;
intra-operatively receiving an input from a user to update the pre-operative plan by positioning the generic virtual boundary to an updated location relative to the virtual anatomical model; and
in response to intra-operatively receiving the input, and while the generic virtual boundary is positioned at the updated location relative to the virtual anatomical model, automatically and intra-operatively performing the following:
computing the intersection of the generic surface and the virtual anatomical model to define the cross-sectional contour of the virtual anatomical model;
morphing the generic edge to the cross-sectional contour to produce the customized surface with the patient-specific edge;
generating the customized face extending from, and along, the patient-specific edge; and
producing the patient-specific virtual boundary by merging the customized surface and the customized face.

14. A non-transitory computer readable medium comprising instructions, which when executed by one or more processors, are configured to:
obtain a generic virtual boundary comprising a generic surface with a generic edge;
position the generic virtual boundary relative to a virtual anatomical model such that the generic surface intersects the virtual anatomical model;

compute an intersection of the generic surface and the virtual anatomical model to define a cross-sectional contour of the virtual anatomical model;

morph the generic edge to the cross-sectional contour to produce a customized surface with a patient-specific edge;

generate a customized face that extends from, and along, the patient-specific edge;

produce a patient-specific virtual boundary by merger of the customized surface and the customized face; and configure the patient-specific virtual boundary to provide a constraint on movement and/or operation of a surgical tool responsive to interaction between the surgical tool and the patient-specific virtual boundary.

15. The non-transitory computer readable medium of claim 14, wherein the generic surface is further defined as a first generic surface and the generic edge is further defined as a first generic edge, and the instructions, when executed by one or more processors, are configured to:

obtain the generic virtual boundary comprising the first generic surface with the first generic edge, and a second generic surface with a second generic edge;

position the generic virtual boundary relative to the virtual anatomical model such that the first generic surface intersects the virtual anatomical model;

compute the intersection of the first generic surface and the virtual anatomical model to define the cross-sectional contour of the virtual anatomical model;

morph the first generic edge to the cross-sectional contour to produce the customized surface with the patient-specific edge;

maintain a geometry of the second generic surface and the second generic edge;

generate the customized face that extends along the patient-specific edge and extends between the patient-specific edge and the second generic edge; and produce the patient-specific virtual boundary by merger of the customized surface, the second generic surface, and the customized face.

16. The non-transitory computer readable medium of claim 14, wherein the generic surface is further defined as a first generic surface and the generic edge is further defined as a first generic edge, and the instructions, when executed by one or more processors, are configured to:

obtain the generic virtual boundary comprising the first generic surface with the first generic edge, and a second generic surface with a second generic edge;

position the generic virtual boundary relative to the virtual anatomical model such that both the first generic surface and the second generic surface intersect the virtual anatomical model;

compute the intersection of the first generic surface and the virtual anatomical model to define a first cross-sectional contour of the virtual anatomical model;

morph the first generic edge to the first cross-sectional contour to produce a first customized surface with a first patient-specific edge;

compute the intersection of the second generic surface and the virtual anatomical model to define a second cross-sectional contour of the virtual anatomical model;

morph the second generic edge to the second cross-sectional contour to produce a second customized surface with a second patient-specific edge;

generate the customized face that extends between, and along, the first patient-specific edge and the second patient-specific edge; and produce the patient-specific virtual boundary by merger of the first customized surface, the second customized surface, and the customized face.

17. The non-transitory computer readable medium of claim 14, wherein the instructions, when executed by one or more processors, are configured to:

morph the generic edge to a contour being similar to the cross-sectional contour and the contour being spaced apart from the cross-sectional contour by an offset distance, and wherein the contour corresponds to the patient-specific edge, and the offset distance is derived from a geometric feature of the surgical tool.

18. The non-transitory computer readable medium of claim 14, wherein the instructions, when executed by one or more processors, are configured to:

obtain a pre-operative plan including the generic virtual boundary having a geometry derived from a virtual implant model, and having the generic virtual boundary positioned at a first location relative to the virtual anatomical model;

receive an intra-operative input from a user to update the pre-operative plan by positioning the generic virtual boundary to an updated location relative to the virtual anatomical model; and in response to receipt of the intra-operative input, and while the generic virtual boundary is positioned at the updated location relative to the virtual anatomical model, automatically and intra-operatively perform the following:

compute the intersection of the generic surface and the virtual anatomical model to define the cross-sectional contour of the virtual anatomical model;

morph the generic edge to the cross-sectional contour to produce the customized surface with the patient-specific edge;

generate the customized face extending from, and along, the patient-specific edge; and produce the patient-specific virtual boundary by merging the customized surface and the customized face.

19. A surgical system comprising:

a surgical tool; and one or more controllers coupled to the surgical tool and being configured to:

obtain a generic virtual boundary comprising a generic surface with a generic edge;

position the generic virtual boundary relative to a virtual anatomical model such that the generic surface intersects the virtual anatomical model;

compute an intersection of the generic surface and the virtual anatomical model to define a cross-sectional contour of the virtual anatomical model;

morph the generic edge to the cross-sectional contour to produce a customized surface with a patient-specific edge;

generate a customized face that extends from, and along, the patient-specific edge;

produce a patient-specific virtual boundary by merger of the customized surface and the customized face; and configure the patient-specific virtual boundary to provide a constraint on movement and/or operation of a surgical tool responsive to interaction between the surgical tool and the patient-specific virtual boundary.

20. The surgical system of claim 19, further comprising a navigation system configured to track the surgical tool and a patient anatomy with which the surgical tool interacts, and wherein the one or more controllers are configured to:
  control the navigation system to register the virtual anatomical model and the patient-specific virtual boundary to a physical anatomy;
  obtain, from the navigation system, tracked states of the surgical tool and the physical anatomy;
  based on the tracked states, detect an interaction between the surgical tool and the patient-specific virtual boundary; and
  in response to the detected interaction, control the surgical tool to constrain movement and/or operation of the surgical tool.

* * * * *